(12) United States Patent
Yoneda et al.

(10) Patent No.: US 7,311,890 B2
(45) Date of Patent: Dec. 25, 2007

(54) PROCESS FOR THE PRODUCTION OF FLUORINATED ORGANIC COMPOUNDS AND FLUORINATING AGENTS

(75) Inventors: Norihiko Yoneda, Sapporo (JP); Tsuyoshi Fukuhara, Sapporo (JP); Kazuhiro Shimokawa, Settsu (JP); Kenji Adachi, Tsukuba (JP); Satoshi Oishi, Tsukuba (JP)

(73) Assignee: Daikin Industries, Ltd., Osaka (JP)

( * ) Notice: Subject to any disclaimer, the term of this patent is extended or adjusted under 35 U.S.C. 154(b) by 518 days.

(21) Appl. No.: 10/885,042

(22) Filed: Jul. 7, 2004

(65) Prior Publication Data

US 2004/0245505 A1    Dec. 9, 2004

Related U.S. Application Data

(62) Division of application No. 10/296,942, filed as application No. PCT/JP01/05017 on Jun. 13, 2001, now Pat. No. 6,784,327.

(30) Foreign Application Priority Data

| Jun. 13, 2000 | (JP) | ............................. 2000-177453 |
| Jul. 13, 2000 | (JP) | ............................. 2000-212447 |
| Sep. 18, 2000 | (JP) | ............................. 2000-281515 |
| Nov. 6, 2000 | (JP) | ............................. 2000-337929 |

(51) Int. Cl.
   *C01B 7/24*    (2006.01)
(52) U.S. Cl. ..................... 423/466; 423/462; 423/483
(58) Field of Classification Search ............... 423/462, 423/466, 483
   See application file for complete search history.

(56) References Cited

U.S. PATENT DOCUMENTS 2,702,306 A    2/1955    Gall et al.
2,918,434 A    12/1959   Gall et al.
2,993,937 A    7/1961    Pavlath
3,283,020 A    11/1966   Parsons ................. 260/653
3,406,214 A    10/1968   Blochl .................. 260/653

FOREIGN PATENT DOCUMENTS

| JP | 58-192837 | 11/1983 |
| JP | 58-192838 | 11/1983 |
| JP | 58-203924 | 11/1983 |
| JP | 59-51225  | 3/1984  |

OTHER PUBLICATIONS

Lewe, T. et al; "Eigenschaften und Reaktionen von Tris(2,6-difluorphenyl)bismut(III)-und Tris(2,6-difluorphenyl)bismut(V)-Verbindungen", Z. anorg. allg. Chem, 623(1997) pp. 122-128.
Frohn, H.J. et al. "Beitrage zur Chemie des Iodpentafluorids Teil V. . . . "; Journal of Fluorine Chemistry, 34 (1986) pp. 129-145.
Frohn, H.J. et al. "Beitrage zur Chemie des Iodpentafluorids Teil IV. . . . "; Journal of Fluorine Chemistry, 34 (1986) pp. 73-82.
International Search Report dated Sep. 4, 2001.
"The Developments and Application of Monofluorinating agents and Trifluoromethylating agents", Organo-fluorine Industry, 1988, pp. 12-14, with English translation.
"Use of Trimethyl amine Tris (hydrogen fluoride)", Shenyang Chemical Engineering (4), 1996, pp. 37-38, with English translation.

*Primary Examiner*—Elvis O. Price
(74) *Attorney, Agent, or Firm*—Kratz, Quintos & Hanson, LLP

(57) ABSTRACT

A process for the production of a fluorinated organic compound, characterized by fluorinating an organic compound having a hydrogen atoms using $IF_5$; and a novel fluorination process for fluorinating an organic compound having a hydrogen atoms by using a fluorinating agent containing $IF_5$ and at least one member selected from the group consisting of acids, bases, salts and additives.

9 Claims, No Drawings

PROCESS FOR THE PRODUCTION OF FLUORINATED ORGANIC COMPOUNDS AND FLUORINATING AGENTS

This is a Divisional Application of U.S. patent application Ser. No. 10/296,942, filed on Dec. 10, 2002, now U.S. Pat. No. 6,784,327, which is a 371 of PCT/JP01/05017, filed on Jun. 13, 2001, which is hereby incorporated by reference.

TECHNICAL FIELD

The present invention relates to a process for fluorinating an organic compound having a hydrogen atom or hydrogen atoms using $IF_5$.

BACKGROUND ART

The following are known as fluorinating agents for fluorinating organic compounds: HF, KF, IF, $IF_5$, tetrabutylammonium fluoride, tris(dimethylamino)sulfur(trimethylsilyl) difluoride (TASF), $SF_4$, diethylaminosulfurtrifluoride (DAST), fluorine gas, $XeF_2$, $CF_3OF$, $CH_3COOF$, $ClO_3F$, N-fluoropyridinium triflate, 1-chloromethyl-4-fluoro-1,4-diazoniabicyclo[2.2.2]octane bis(tetrafluoroborate), 1-hydroxy-4-fluoro-1,4-diazoniabicyclo[2.2.2]octane bis(tetrafluoroborate), N-fluorobenzenesulfonimide, etc. (Sheppard, W. A.; Sharts, C. M. Organic Fluorine Chemistry, 1969, W. A. Benjamin: Chambers, R. D.; Fluorine in Organic Chemistry, 1973, Wiley-Interscience: Hudlicky, M. Chemistry of Organic Fluorine Compounds, 1976, Ellis Horwood: Hudlicky; M. and Pavlath, A. E., Chemistry of Organic Fluorine Compounds II, 1995, ACS Monograph 187: N. Ishikawa and Y. Kobayashi, Fluorinated compounds-Chemistry and their application, 1979, Kodansha Ltd.: Outline of chemistry/New fluorine chemistry, 1980, Japan Scientific Societys Press: N. Ishikawa, T. Kitazume, and A. Takaoka, Journal of the Society of Synthetic Organic Chemistry, 1979, 37, 606: T. Umemoto, Journal of the Society of Synthetic Organic Chemistry, 1992, 50, 338: S. D. Taylor, C. C. Kotoris, and G. Hum; Tetrahedron, 1999, 55, 12431: Japanese Unexamined Patent Publication No. 1997-227531, etc.)

Among those fluorinating agents, HF, KF, IF, tetrabutylammonium fluoride, and sulfoniumsilicate (TASF) have low reactivity, and therefore have limited uses. $SF_4$ is a toxic gas having a boiling point at $-40.4°$ C., which is difficult to handle. Fluorine gas is so active that it is difficult to control its reaction. Furthermore, it is reported that $CF_3OF$, $CH_3COOF$, and $ClO_3F$ are explosive gases and should be handled with caution. Diethylaminosulfurtrifluoride (DAST), $XeF_2$, N-fluoropyridinium triflate, 1-chloromethyl-4-fluoro-1,4-diazoniabicyclo[2.2.2]octane bis(tetrafluoroborate), 1-hydroxy-4-fluoro-1,4-diazoniabicyclo[2.2.2]octane bis(tetrafluoroborate), N-fluorobenzenesulfonimide, etc., are easy to handle and enable selective fluorination; however, they are expensive reagents and this causes a problem in using them for industrial purposes.

$IF_5$ is an industrially usable fluorinating agent that is a nonexplosive and easy-to-handle liquid having a boiling point at $100.5°$ C. and a melting point at $9.4°$ C. Fluorination using $IF_5$ is employed only in a process of adding IF to perfluoroolefin and substituting iodine of the perfluoroiodoolefin with fluorine (M. Sakai, Organic Fluorine Chemistry I, 1970, pp 348-351, GIHODO SHUPPAN Co., Ltd.: A. A. Banks, H. J. Haszeldine, and V. Kerrigan, J. Chem. Soc., 1948, 2188: R. D. Chambers, W. K. R. Musgrave, and J. Savory, J. Chem. Soc., 1961, 3779). However, since it is difficult to control its high oxidizing property, using $IF_5$ for fluorinating organic compounds that have hydroxyl groups, carbonyl groups, etc., was hitherto not known.

DISCLOSURE OF THE INVENTION

The inventors of the present invention conducted extensive research on the above problems. Consequently, they found that various kinds of organic compounds having hydrogen atoms could be fluorinated by using $IF_5$.

Specifically, the present invention relates to the following Items 1 to 12.

Item 1. A method for producing a fluorinated organic compound by fluorinating an organic compound having hydrogen atoms in the presence of $IF_5$.

Item 2. The method for producing a fluorinated organic compound according to Item 1, wherein the organic compound having hydrogen atoms is fluorinated in the presence of $IF_5$ and HF.

Item 3. The production method according to Item 1, wherein the organic compound having hydrogen atoms is reacted in the presence of $IF_5$, HF, and an organic base and/or a room temperature molten salt.

Item 4. The production method according to Item 1, wherein the organic compound having hydrogen atoms is reacted in the presence of $IF_5$ and a room temperature molten salt.

Item 5. The production method according to Item 1, wherein the fluorination reaction does not comprise substitution of bromine or iodine with fluorine, nor an addition reaction of iodine fluoride (IF) to a double bond or triple bond.

Item 6. The production method according to Item 5, wherein the fluorination reaction is conducted in the presence of $IF_5$ and at least one member selected from the group consisting of acids, salts, and additives.

Item 7. The production method according to Item 5, wherein the fluorination reaction is conducted in the presence of $IF_5$ and at least one member selected from the group consisting of bases, salts, and additives.

Item 8. A fluorinating agent for use in fluorinating an organic compound having hydrogen atoms, which comprises $IF_5$, HF, and an organic base and/or a room temperature molten salt.

Item 9. A fluorinating agent for use in fluorinating an organic compound having hydrogen atoms, which comprises $IF_5$ and a room temperature molten salt.

Item 10. A fluorinating agent for use in fluorinating an organic compound having hydrogen atoms, which comprises $IF_5$ and at least one member selected from the group consisting of acids, salts, and additives.

Item 11. A fluorinating agent for use in fluorinating an organic compound having hydrogen atoms, which comprises $IF_5$ and at least one member selected from the group consisting of bases, salts, and additives.

Item 12. A fluorinating agent for use in fluorinating an organic compound having hydrogen atoms, which comprises $IF_5$, HF, and triethylamine.

In the present invention, examples of a organic compound having hydrogen atoms include; compounds having an OH group; ketones (including diketone, β-ketocarboxylic acid, β-ketoester); aldehydes; Schiff base, hydrazone and like imines; esters; sulfides; olefins or epoxy; aromatic compounds (phenylhydrazine derivatives, phenol derivatives, 2-naphthol derivatives, aniline derivatives); and thiocarbonyl compounds, etc.

In fluorine substitution in a organic compound having hydrogen atoms, the following atom and groups are substituted with fluorine: hydrogen atom (CH→CF), carbonyl group (CO→CF$_2$), hydrazino group (Ph—NHNH$_2$→Ph—F; C=N—NH$_2$→CF$_2$), hydroxyl group (C—OH→C—F), epoxy group (C—O—→C—F), etc.

(1) Compounds Having an OH Group

The following reactions are exemplified:

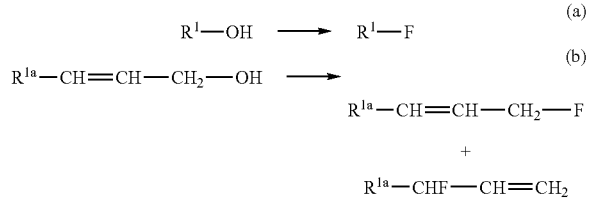

[in the above formulas, $R^1$ represents an alkyl group that may have a substituent, an aralkyl group that may contain a substituent, an alkenyl group that may contain a substituent, an acyl group that may contain a substituent, a cycloalkyl group that may contain a substituent, a heterocycloalkyl group that may contain a substituent, or a mono-, di- or tri-saccharide that may contain a protecting group. $R^{1a}$ represents an alkyl group that may contain a substituent, an aryl group that may contain a substituent, an aralkyl group that may contain a substituent, an alkenyl group that may contain a substituent, an acyl group that may contain a substituent, a cycloalkyl group that may contain a substituent, a heterocycloalkyl group that may contain a substituent, or a mono-, di- or tri-saccharide that may contain a protecting group.]

In the present specification, "may contain a substituent" includes both cases where a substituent is contained and not contained. For example, an alkyl group that may contain a substituent includes alkyl groups and alkyl groups having a substituent.

Specific examples of compounds having an OH group include apliphatic alcohols, such as methanol, ethanol, n-propanol, isopropanol, n-butanol, isobutanol, tert-butanol, pentanol, hexanol, octanol, decanol, palmityl alcohol, stearyl alcohol, oleyl alcohol, etc., alicyclic alcohols, such as benzyl alcohol, a mono-, di- or tri-saccharide having at least one non-protected hydroxyl group, cyclohexyl alcohol, ascorbic acid, etc., steroid alcohols, such as cholesterol, cholic acid, cortisone, etc.; and carboxylic acids, such as acetic acid, trifluoroacetic acid, propionic acid, acrylic acid, methacrylic acid, crotonic acid, butyric acid, valeric acid, isovaleric acid, pivalic acid, lauric acid, myristic acid, palmitic acid, stearic acid, oleic acid, linoleic acid, linolenic acid, cinnamic acid and like aliphatic mono-carboxylic acids, oxalic acid, succinic acid, malonic acid, glutaric acid, adipic acid, maleic acid, fumaric acid, citric acid and like polycarboxylic acids, benzoic acid, salicylic acid, (o-,m-,p-)phthalic acid, nalidixic acid, nicotinic acid and like aromatic carboxylic acids, pantothenic acid, biotin and like vitamins having carboxylic acid groups, glycine, alanine, phenylalanine, cysteine, aspartic acid, glutamic acid, threonine, histidine, lysine, methionine, proline and like 20 kinds of natural amino acids, lactic acid, citric acid, malic acid, tartaric acid and like hydroxycarboxylic acids.

(2) Ketones (Including Diketone, β-Ketocarboxylic Acid, β-Ketoester), Aldehydes, Imines, Such as Schiff Base, Hydrazone, Etc., and Esters The following reactions are exemplified:

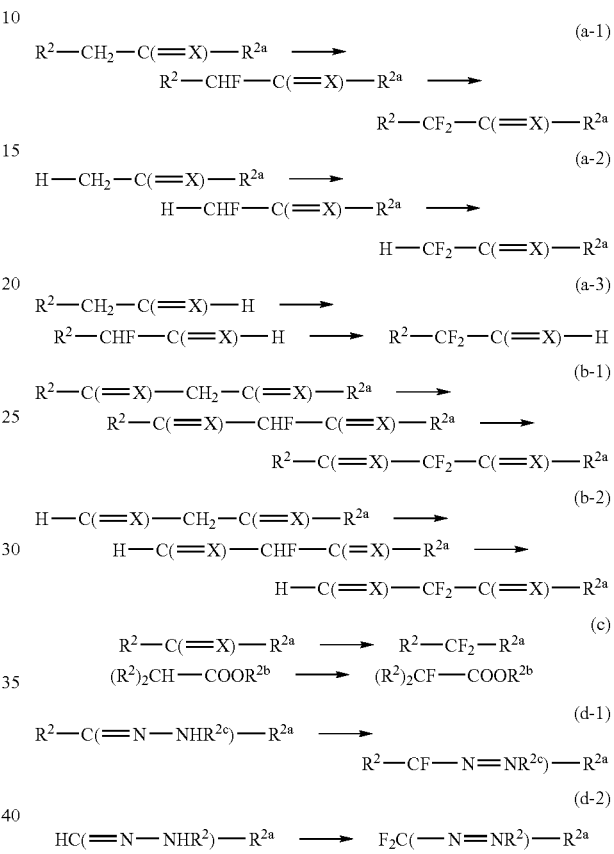

[in the above formulas, X represents O or NR' (R' represents a hydrogen atom, an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, a heterocyclic group that may contain a substituent, an alkoxy group that may contain a substituent, an aryloxy group that may contain a substituent, an amino group, a monoalkylamino group that may contain a substituent, a dialkylamino group that may contain a substituent, an acyl group that may contain a substituent, or an acylamino group that may contain a substituent). $R^2$, $R^{2a}$, and $R^{2c}$ may be the same or different and each represents a hydrogen atom, an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, a heterocyclic group that may contain a substituent, an alkoxy group that may contain a substituent, an aryloxy group that may contain a substituent, a monoalkylamino group that may contain a substituent, a dialkylamino group that may contain a substituent, an acyl group that may contain a substituent, or an acylamino group that may contain a substituent. $R^2$ and $R^{2a}$ may bond to each other and form a ring structure. $R^{2b}$ represents an alkyl group that may contain a substituent, an aralkyl group that may contain a substituent, or an aryl group that may contain a substituent.]

Examples of substances having a ring structure include 4-membered rings, 5-membered rings, 6-membered rings, and 7-membered rings of aliphatic compounds that may contain a substitute, etc.

Examples of ketones include acetone, methyl ethyl ketone, acetylacetone, acetoacetic acid, acetoacetate, cyclohexanone, acetophenone, benzophenone, propiophenone, 4-piperidone, 1-oxo-1,2-dihydronaphthalene, benzylideneacetophenone (chalcone), deoxybenzoin, and ketals thereof, etc.

Examples of aldehydes include acetoaldehyde, propionaldehyde, buthylaldehyde, isobutylaldehyde, valeraldehyde, isovaleraldehyde, acrylaldehyde, benzaldehyde, cinnamaldehyde, anisaldehyde, nicotinealdehyde, or acetals thereof, etc.

Examples of imines of Schiff base, hydrazone and the like include condensates of ketone or aldehyde with an appropriate primary amine.

(3) Sulfides (Including Dithioacetal and Dithioketal)

One or two hydrogen atoms of methylene that is located adjacent to a sulfur atom are substituted with fluorine atoms, or a sulfur atom is substituted with fluorine:

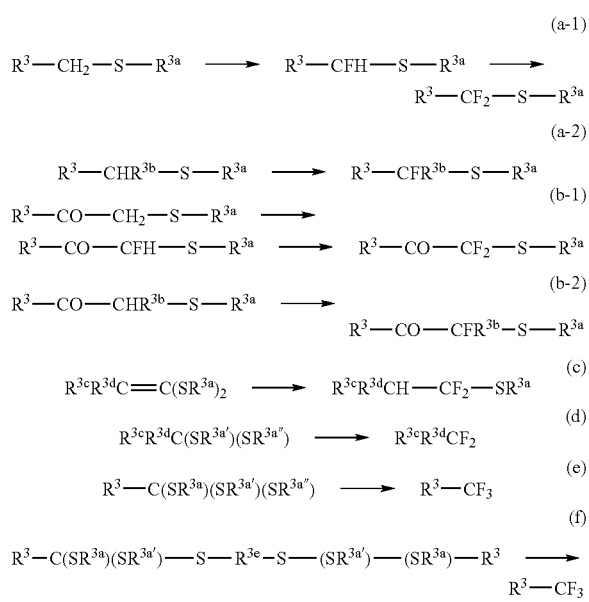

[in the above formulas, $R^{3a}$, $R^{3a'}$, and $R^{3a''}$ may be the same or different and each represents an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, a heterocyclic group that may contain a substituent, or $R^{3a}$ and $R^{3a'}$ bond to each other and represent a 4-membered ring, 5-membered ring, 6-membered ring, or 7-membered ring of an aliphatic that may contain a substituent. $R^3$ and $R^{3b}$ represent an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, a heterocyclic group that may contain a substituent, an alkoxy group that may contain a substituent, an aryloxy group that may contain a substituent, an amino group, a monoalkylamino group that may contain a substituent, a dialkylamino group that may contain a substituent, an acyl group that may contain a substituent, an acylamino group that may contain a substituent, a cyano group, an alkylsulfinyl group that may contain a substituent, an aralkylsulfinyl group that may contain a substituent, an arylsulfinyl group that may contain a substituent, a cycloalkylsulfinyl group that may contain a substituent, a heterocycloalkylsulfinyl group that may contain a substituent, a sulfinyl group bonded by a heterocyclic group that may contain a substituent, an alkylsulfonyl group that may contain a substituent, an aralkylsulfonyl group that may contain a substituent, an arylsulfonyl group that may contain a substituent, a cycloalkylsulfonyl group that may contain a substituent, a heterocycloalkylsulfonyl group that may contain a substituent, or a sulfonyl group bonded by a heterocyclic group that may contain a substituent. Alternately, $R^3$ and $R^{3b}$ may form 4 to 8-membered rings with carbon atoms with or without having a heteroatom in the ring. In the rings, they may be substituted with a halogen atom, an oxo group, an alkyl group that may contain a substituent, an aralkyl group that may contain a substituent, an aryl group that may contain a substituent, an alkenyl group that may contain a substituent, a cyano group, or an amino group. $R^{3c}$ and $R^{3d}$ represent a hydrogen atom, an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, a heterocyclic group that may contain a substituent, an alkoxy group that may contain a substituent, an aryloxy group that may contain a substituent, a monoalkylamino group that may contain a substituent, a dialkylamino group that may contain a substituent, an acyl group that may contain a substituent, or an acylamino group that may contain a substituent. Alternately, $R^{3c}$ and $R^{3d}$ may form a 4-membered ring, 5-membered ring, 6-membered ring or 7-membered ring of an aliphatic that may contain a substituent, or $R^{3c}$, $R^{3d}$, and C may form

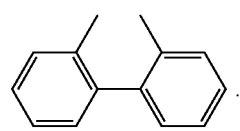

$R^{3e}$ represents an alkylene group or an arylene group.]

Examples of sulfides include methyl ethyl sulfide, methyl benzyl sulfide, 2-phenylthioacetate, 2-phenylthioacetophenone, $C_6H_5$—CO—$CH_2SCH_3$, bis(methylthio)methylbenzene, 2-octyl-1,3-dithiane, 2-phenyl-2-trifluoromethyl-1,3-dithiolane, tris(ethylthio)hexane, 4-tris(methylthio)toluene, etc.

(4) Olefins or Epoxies

The following fluorine addition reactions are exemplified:

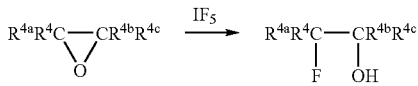

[in the above formula, $R^4$, $R^{4a}$, $R^{4b}$, and $R^{4c}$ each represent a hydrogen atom, an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, or a heterocyclic group that may contain a substituent.]

Examples of epoxies include oxirane, 1,2-epoxyethylbenzene, 1-chloro-2,3-epoxypropane, α,α'-epoxybibenzyl, etc.

(5) Aromatic Compounds

A fluorine substituent is introduced in an aromatic ring by the following reaction. Fluorination of an aromatic ring in a phenol derivative or aniline derivative can be carried out by fluorinating it using $IF_5$ or the like, then reducing it by zinc powder or like reducing agents, to obtain the targeted fluorine compound.

(5-1) Phenylhydrazine Derivatives

A phenylhydrazine residue that may contain a substituent can be substituted with a fluorine atom.

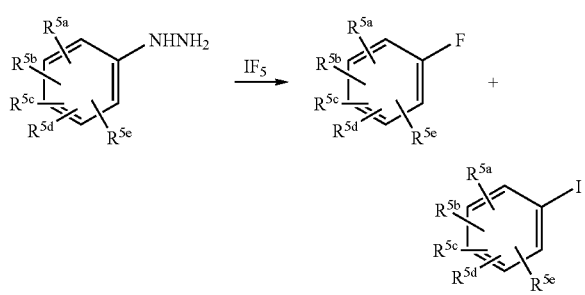

[in the above formula, $R^{5a}$, $R^{5b}$, $R^{5c}$, $R^{5d}$, and $R^{5e}$ each represents a hydrogen atom, an alkyl group, an aralkyl group, an aryl group, an alkoxy group, a nitro group, a cyano group, a halogen atom, an acyl group, an amino group, a monoalkylamino group, a dialkylamino group, an acylamino group, or an alkylthio group.]

(5-2) Phenol Derivatives

A phenol derivative forms the difluorinated quinonoid structure as shown below by reacting with $IF_5$. Thereafter, by reducing the resultant compound, a phenol derivative having fluorine introduced in the ortho- or para-position is produced.

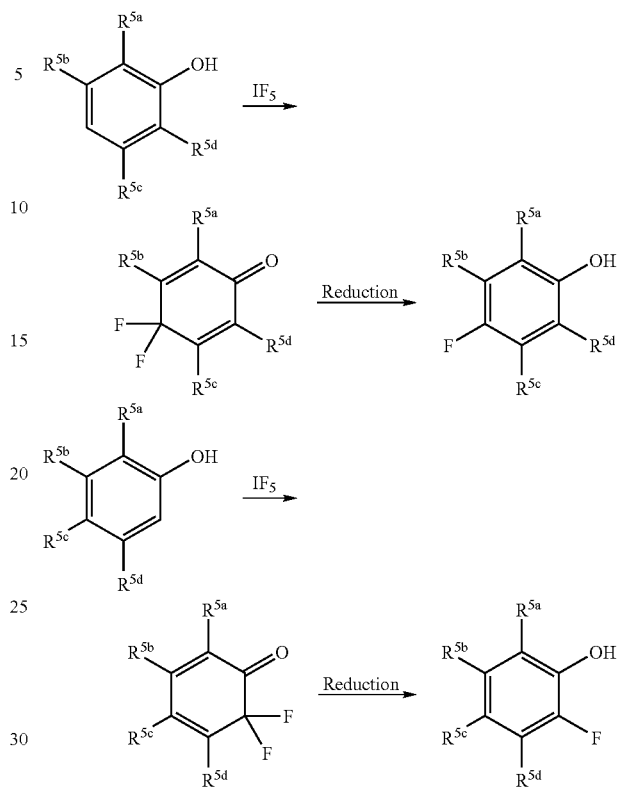

[in the above formulas, $R^{5a}$, $R^{5b}$ $R^{5c}$ and $R^{5d}$ each represents a hydrogen atom, an alkyl group, an aralkyl group, an aryl group, an alkoxy group, a nitro group, a cyano group, a halogen atom, an acyl group, an amino group, a monoalkylamino group, a dialkylamino group, an acylamino group, or an alkylthio group.]

In a starting material in which all atoms or groups in the ortho- and para-positions are substituted, fluorine atoms are introduced into the ortho- or para-position, forming compounds having a fluorine quinonoid structure (e.g., Example 47).

In the above example, phenol that may contain a substituent is used as a phenol derivative; however, it is also possible to introduce fluorine atoms into benzene-based aromatic compounds or condensed polycyclic hydrocarbons that may be substituted and have electron-releasing groups such as a hydroxyl group, an alkoxy group, etc.

(5-3) 2-naphthol Derivatives

A carbon atom in the 1-position of naphthol can be subjected to mono- or di-fluorination.

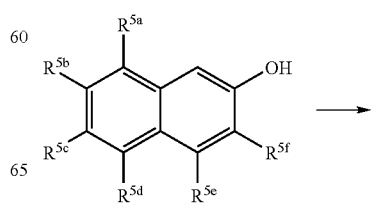

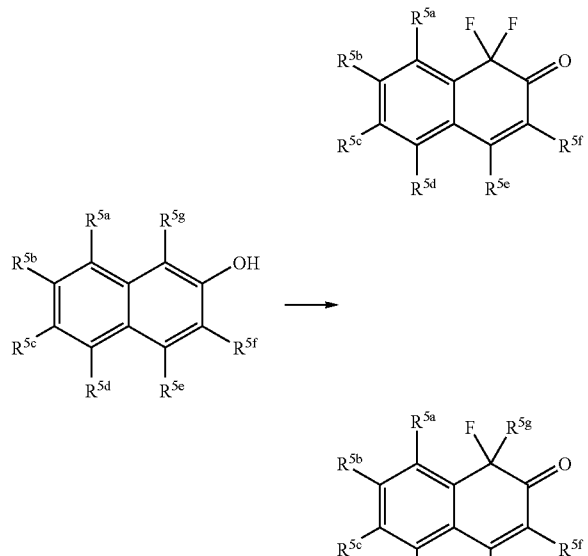

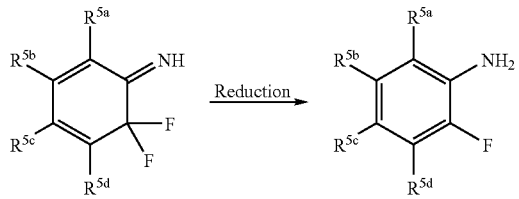

[in the above formulas, $R^{5a}$, $R^{5b}$, $R^{5c}$, $R^{5d}$, $R^{5e}$, $R^{5f}$, and $R^{5g}$ may be the same or different and each represents a hydrogen atom, an alkyl group, an aralkyl group, an aryl group, an alkoxy group, a nitro group, a cyano group, a halogen atom, an acyl group, an amino group, a monoalkylamino group, a dialkylamino group, an acylamino group, or an alkylthio group.]

(5-4) Aniline Derivatives

Similar to a phenol derivative, an aniline derivative forms the difluorinated quinonoid structure as shown below by reacting with $IF_5$. Then, by reducing the resultant compound, an aniline derivative having fluorine introduced in the ortho- or para-position is produced.

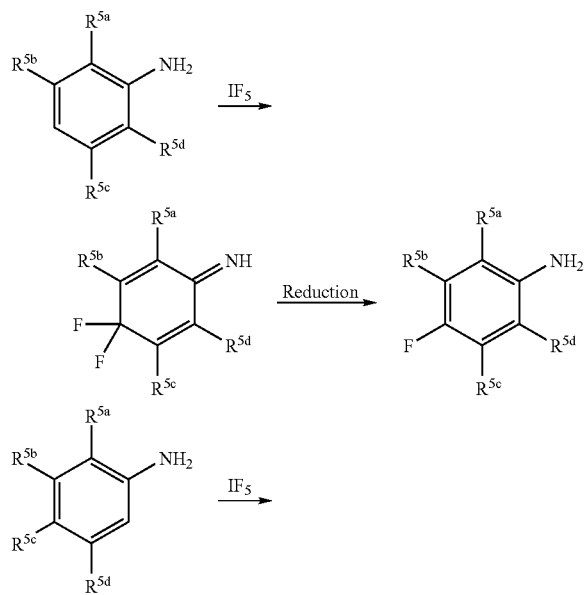

[in the above formulas, $R^{5a}$, $R^{5b}$, $R^{5c}$, and $R^{5d}$ each represents a hydrogen atom, an alkyl group, an aralkyl group, an aryl group, an alkoxy group, a nitro group, a cyano group, a halogen atom, an acyl group, an amino group, a monoalkylamino group, a dialkylamino group, an acylamino group, or an alkylthio group.]

Using aniline that may contain a substituent or naphthylamine that may contain a substituent as an aniline derivative also allows introducing a fluorine atom in an aromatic ring.

(6) Thiocarbonyl Compounds (Including Thioketone, Thioester, Thiocarbonic Ester, Thioamide, Dithiocarboxylate, and Dithiocarbamate)

The following reactions are exemplified:

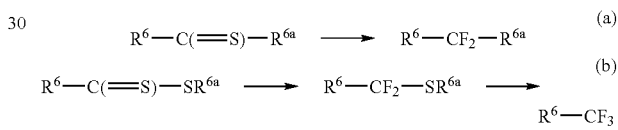

[in the above formulas, $R^6$ and $R^{6a}$ may be the same or different and each represents a hydrogen atom, an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, a heterocyclic group that may contain a substituent, an alkoxy group that may contain a substituent, an aryloxy group that may contain a substituent, a monoalkylamino group that may contain a substituent, a dialkylamino group that may contain a substituent, an acyl group that may contain a substituent, or an acylamino group that may contain a substituent. $R^6$ and $R^{6a}$ may bond to each other and form a ring structure. $R^{6b}$ represents an alkyl group that may contain a substituent, an aralkyl group that may contain a substituent, an aryl group that may contain a substituent, an alkenyl group that may contain a substituent, a cycloalkyl group that may contain a substituent, a heterocycloalkyl group that may contain a substituent, or a heterocyclic group that may contain a substituent.]

Examples of thiocarbonyl compounds include O-methyl cyclohexanecarbothioate, O-propyl 1-piperidinecarbothioate, methyl dithiobenzoate, thiobenzophenone, O-phenyl thiobenzoate, N,N-dimethylphenylthioamide, ethyl 3-quinolinedithiocarboxylate, trifluoromethane carbothioylnaphthalene, N-methyl-N-phenyl trifluoromethanethioamide, N-benzyl-N-phenylheptafluoropropanethioamide,

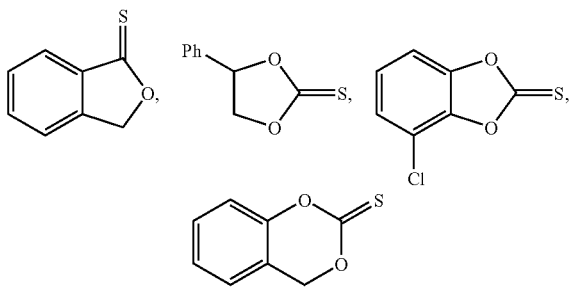

etc.

Examples of alkyl groups include methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and like $C_1$-$C_{18}$ alkyl groups having straight chains or branched chains, preferably methyl, ethyl, n-propyl, isopropyl, n-butyl, isobutyl, sec-butyl, tert-butyl, pentyl, hexyl and like $C_1$-$C_6$ alkyl groups having straight chains or branched chains.

Examples of alkoxy groups include methoxy, ethoxy, n-propoxy, isopropoxy, n-butoxy, isobutoxy, sec-butoxy, tert-butoxy, pentyloxy, hexyloxy and like $C_1$-$C_6$ alkoxy groups having straight chains or branched chains.

Examples of alkenyl groups include a vinyl group, an allyl group, a 3-butenyl group and like $C_2$-$C_6$ alkenyl groups, etc.

Examples of halogens include a fluorine atom, a chlorine atom, a bromine atom, an iodine atom, etc.

Examples of aryl groups include a phenyl group, a naphthyl group, etc.

Examples of aryloxy groups include a phenoxy group, a naphthyloxy group, etc.

Examples of aralkyl groups include 2-phenylethyl, benzyl, 1-phenylethy, 3-phenylpropyl, 4-phenylbutyl and like $C_1$-$C_{10}$ aralkyl groups, etc.

Examples of cycloalkyl groups include cyclopropyl, cyclobutyl, cyclopentyl, cyclohexyl, cycloheptyl, cyclooctyl and like $C_3$-$C_8$ cycloalkyl groups, etc. Preferable are $C_3$-$C_7$ cycloalkyl groups.

Examples of heterocycloalkyl groups include substances in which one or more carbon atoms forming the above described ring structure of cycloalkyl groups are substituted with atoms of nitrogen, oxygen, sulfur, etc.

Examples of monoalkylamino groups include amino groups mono-substituted with the above-described $C_1$-$C_6$ alkyl groups.

Examples of dialkylamino groups include dimethylamino, diethylamino, di-n-propylamino, diisopropylamino, dibutylamino, dipentylamino, dihexylamino and like amino groups di-substituted with the above-described $C_1$-$C_6$ alkyl groups.

Examples of acylamino groups include formylamino, benzoylamino, acetylamino, propionylamino, n-butyrylamino and like $C_1$-$C_8$ acylamino groups.

Examples of alkylthio groups include —S—($C_1$-$C_6$ alkyl groups), etc. ($C_1$-$C_6$ alkyl groups are the same as described above.)

Examples of heterocyclic groups include piperidyl, furyl, thienyl, imidazolyl, oxazolyl, thiazolyl, pyrrolyl, pyrrolidinyl, triazolyl, benzothiazolyl, benzoimidazolyl, oxadiazolyl, thiadiazolyl, indolyl, pyrazolyl, pyridazinyl, cinnolinyl, quinolinyl, isoquinolinyl, quinoxalinyl, pyradinyl, pyridyl, benzofuryl, benzothienyl, tetrazolyl, etc.

Examples of acyl groups include formyl, acetyl, propionyl, n-butyryl, isobutyryl, valeryl, isovaleryl, pivaloyl and like $C_{1-6}$ acyl groups having straight chains or branched chains, benzoyl and a substituted acyl group.

Specific examples of an alkyl group, an aralkyl group, an aryl group, a cycloalkyl group, a heterocycloalkyl group, and a heterocyclic group in an alkylsulfinyl group, an aralkylsulfinyl group, an arylsulfinyl group, a cycloalkylsulfinyl group, a heterocycloalkylsulfinyl group, and a sulfinyl group having a heterocyclic group bonded thereto are as described above.

Specific examples of an alkyl group, an aralkyl group, an aryl group, a cycloalkyl group, a heterocycloalkyl group, and a heterocyclic group in an alkylsulfonyl group, an aralkylsulfonyl group, an arylsulfonyl group, a cycloalkylsulfonyl group, a heterocycloalkylsulfonyl group, and a sulfonyl group having a heterocyclic group bonded thereto are as described above.

The number of substituents in an alkyl group having substituents, an alkoxy group having substituents, or an alkenyl group having substituents is generally 1 to 5, and preferably 1 to 3. Examples of substituents include halogen, $C_1$-$C_6$ alkoxy, $C_1$-$C_6$ alkylthio, cyano, nitro, an amino group, a hydroxyl group and the like. Examples of an alkyl group having halogens include an alkyl group in which one or more hydrogen atoms are substituted with fluorine.

The number of substituents in an aralkyl group having substituents, an aryl group having substituents, an aryloxy group having substituents, a cycloalkyl group having substituents, a heterocycloalkyl group having substituents, a heterocyclic group having substituents, a monoalkylamino group having substituents, a dialkylamino group having substituents, an acylamino group having substituents, an alkylsulfinyl group having substituents, an aralkylsulfinyl group having substituents, an arylsulfinyl group having substituents, a cycloalkylsulfinyl group having substituents, a heterocycloalkylsulfinyl group having substituents, a sulfinyl group to which a heterocyclic group having substituents is bonded, an alkylsulfonyl group having substituents, an aralkylsulfonyl group having substituents, an arylsulfonyl group having substituents, a cycloalkylsulfonyl group having substituents, a heterocycloalkylsulfonyl group having substituents, or a sulfonyl group to which a heterocyclic group having substituents is bonded is generally 1 to 5, preferably 1 to 3. Examples of substituents include $C_1$-$C_6$ alkyl groups, a halogen atom, $C_1$-$C_6$ alkoxy groups, $C_1$-$C_6$ alkylthio groups, cyano, nitro, an amino group, a hydroxyl group and the like.

The number of substituents in a 4- to 7-membered ring of aliphatics having substituents is generally 1 to 5, and preferably 1 to 3. Examples of substituents include $C_1$-$C_6$ alkyl groups, a halogen atom, $C_1$-$C_6$ alkoxy groups, $C_1$-$C_6$ alkylthio groups, cyano, nitro, an amino group, a hydroxyl group, carboxy ester and the like. In addition,

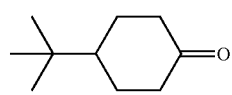

is also included in 4- to 7-membered ring of aliphatics having substituents.

Examples of acyl groups having substituents include a chloroacetyl group, a bromoacetyl group, a dichloroacetyl group, a trifluoroacetyl group and like substituted acetyl groups, a methoxyacetyl group, an ethoxyacetyl group and like acetyl groups substituted with alkoxy groups, a methylthioacetyl group and like acetyl groups substituted with alkylthio groups, a phenoxyacetyl group, a phenylthioacetyl group, a 2-chlorobenzoyl group, a 3-chlorobenzoyl group, a 4-chlorobenzoyl group, a 4-methylbenzoyl group, a 4-t-butylbenzoyl group, a 4-methoxybenzoyl group, a 4-cyanobenzoyl group, a 4-nitrobenzoyl group and like substituted benzoyl groups, etc.

As for the production method and fluorinating agents of the present invention, it is preferable to use, in addition to $IF_5$, 1 to 4 members and preferably 1 to 3 members selected from the group consisting of acids, bases, salts and additives. More preferably, 1 to 3 members except for the combination of an acid, a basic and a salt are used.

Specific examples of acids include sulfuric acid, nitric acid, phosphoric acid, polyphosphoric acid, hydrogen fluoride, fluoric acid, hydrochloric acid, hydrogen bromide, hydrogen iodide, hypochlorous acid, chlorous acid, chloric acid, perchloric acid, perbromic acid, periodic acid and like hydrogen halides, or hydrohalic acid, hypohalous acid, halous acid, halogen acid, and perhalogen acid;

fluorosulfonic acid, chlorosulfonic acid, methanesulfonic acid, ethanesulfonic acid, trifluoromethanesulfonic acid, difluoromethanesulfonic acid, trichloromethanesulfonic acid, perfluorobutanesulfonic acid, perfluorooctanesulfonic acid, benzenesulfonic acid, toluenesulfonic acid, nitrobenzenesulfonic acid and like sulfonic acids, or polystyrenesulfonic acid, fluorinated sulfonic acid resin (Nafion-H) and like polymer carrying sulfonic acids;

formic acid, acetic acid, propionic acid, chloroacetic acid, bromoacetic acid, dichloroacetic acid, trichloroacetic acid, trifluoroacetic acid, glycolic acid, lactic acid, benzoic acid, oxalic acid, succinic acid and like mono- or poly-carboxylic acids;

$SO_3$, $BF_3$, $BCl_3$, $B(OCH_3)_3$, $AlCl_3$, $AlBr_3$, $SbF_3$, $SbCl_3$, $SbF_5$, $PF_3$, $PF_5$, $AsF_3$, $AsCl_3$, $AsF_5$, $TiCl_4$, $NbF_5$, $TaF_5$ and like Lewis acids or their ether complexes;

$HBF_4$, $HPF_6$, $HAsF_6$, $HSbF_6$, $HSbCl_6$ and like acids formed between Lewis acids and hydrogen halides, or their ether complexes;

or mixtures of two or more members described above. The acids used here may be supported by several kinds of carriers. Examples of carriers include $SiO_2$, methylated $SiO_2$, $Al_2O_3$, $Al_2O_3$—WB, $MoO_3$, $ThO_2$, $ZrO_2$, $TiO_2$, $Cr_2O_3$, $SiO_2$—$Al_2O_3$, $SiO_2$—$TiO_2$, $SiO_2$—$ZrO_2$, $TiO_2$—$ZrO_2$, $Al_2O_3$—$B_2O_3$, $SiO_2$—$WO_3$, $SiO_2$—$NH_4F$, $HSO_3Cl$—$Al_2O_3$, HF—$NH_4$—Y, HF—$Al_2O_3$, $NH_4F$—$SiO_2$—$Al_2O_3$, $AlF_3$—$Al_2O_3$, Ru—F—$Al_2O_3$, F—$Al_2O_3$, KF—$Al_2O_3$, $AlPO_4$, $AlF_3$, bauxite, kaolin, activated carbon, graphite, Pt-graphite, ion-exchange resin, metal sulfate, chloride, Al and like metals, Al—Mg, Ni—Mo and like alloys, polystyrene and like polymers, etc.

The amount of the above-described acids used in the present invention can be selected from a catalytic amount to an excessive amount. The preferable amount is 0.01 to 100 moles, and more preferably 0.1 to 20 moles per mole of the organic compound containing a hydrogen atom to be fluorinated. It is also possible to use the above-described acids as a reaction solvent. In this case, the amount of solvent used can be selected from little to excessive.

The bases or organic bases used in the present invention include the ones generally used, such as sodium hydroxide, potassium hydroxide, lithium hydroxide, rubidium hydroxide, cesium hydroxide, magnesium hydroxide, calcium hydroxide, barium hydroxide and like hydroxides of alkali metals or alkaline earth metals;

sodium methoxide, sodium ethoxide, sodium butoxide, potassium methoxide, potassium ethoxide, potassium butoxide, lithium methoxide, lithium ethoxide and like alkali metal alkoxides;

sodium hydride, potassium hydride, lithium hydride, calcium hydride and like hydrides of alkali metals or alkaline earth metals;

sodium, potassium, lithium and like alkali metals;

magnesium oxide, calcium oxide and like alkaline earth metal oxides;

ammonia, ammonium hydroxide, tetramethylammonium hydroxide, tetraethylammonium hydroxide, tetrabuthylammonium hydroxide, octyltriethylammonium hydroxide, benzyltrimethylammonium hydroxide and like ammonium hydroxide salts, or AMBERLITE® resin and like polymer carrying ammonium hydroxide salts, etc.;

aliphatic amine (primary amine, secondary amine, tertiary amine), alicyclic amine (secondary amine, tertiary amine), aromatic amine (primary amine, secondary amine, tertiary amine), heterocyclic amine and like organic bases; and mixtures thereof.

Specific examples of aliphatic primary amines include methylamine, ethylamine, propylamine, butylamine, pentylamine, hexylamine, cyclohexylamine, ethylenediamine, etc. Specific examples of aliphatic secondary amines include dimethylamine, diethylamine, dipropylamine, dibutylamine, dipentylamine, dihexylamine, dicyclohexylamine, etc. Specific examples of aliphatic tertiary amines include trimethylamine, triethylamine, diisopropylethylamine, N,N,N',N'-tetramethylethylenediamine, etc.

Specific examples of alicyclic secondary amines include piperidine, piperazine, pyrrolidine, morpholine, etc. Specific examples of alicyclic tertiary amines include N-methylpiperazine, N-methylpyrrolidine, 5-diazabicyclo[4.3.0]nonane-5-ene, 1,4-diazabicyclo[2.2.2]octane, etc.

Specific examples of aromatic amines include aniline, methylaniline, dimethylaniline, N,N-dimethylaniline, haloaniline, nitroaniline, etc.

Specific examples of heterocyclic amines include pyridine, pyrimidine, piperazine, quinoline, imidazole, etc., and further include polyaryl amine, polyvinylpyridine and like polymer carrying amine compounds, etc., and mixtures thereof.

The amount of the above-described bases used in the present invention can be selected from a catalytic amount to an excessive amount. The preferable amount of the bases used is 0.01 to 20 moles, and more preferably 0.1 to 10 moles per mole of the organic compound containing a hydrogen atom to be fluorinated.

In the present invention, when an acid as a reaction solvent, and a metal, metal hydroxide, metal hydride, metal alkoxide, metal oxide, or organic base as a base are used, a metal salt of an acid or a salt of an organic base is naturally produced from a reaction between the acid and base.

The salts used in the present invention are compounds generated by a reaction between an acid and a base, and mainly include the compounds obtained by the reaction between the above-mentioned acids and bases.

For example, metal salts or ammonium salts of sulfuric acids or sulfonic acids, such as sodium sulfate, sodium hydrogensulfate, potassium sulfate, potassium hydrogensulfate, lithium sulfate, cesium sulfate, calcium sulfate, magnesium sulfate, ammonium sulfate, triethylammonium sulfate, pyridinium sulfate, trimethylpyridinium sulfate, polyarylammonium sulfate, polyvinylpyridinium sulfate, sodium methanesulfonate, ammonium methanesulfonate, tetramethylammonium methanesulfonate, potassium ethanesulfonate, lithium butanesulfonate, sodium benzenesulfonate, sodium toluenesulfonate, sodium trifluoromethanesulfonate, sodium polystyrenesulfonate, etc.;

sodium formate, ammonium formate, sodium acetate, potassium acetate, lithium acetate, magnesium acetate, calcium acetate, ammonium acetate, methylammonium acetate, diethylammonium acetate, triethylammonium acetate, tetraethylammonium acetate, pyridinium acetate, sodium propionate, potassium propionate, sodium butyrate, polyarylammonium butyrate, polyvinylpyridinium acetate, sodium isobutyrate, sodium valerianate, sodium nonanoate, sodium chloroacetate, sodium bromoacetate, sodium trichloroacetate, sodium trifluoroacetate, sodium glycolate, sodium lactate, sodium benzoate, sodium oxalate, sodium succinate, sodium polyacrylate and like metal salts or ammonium salts of carboxylic acids;

LiBr, LiI, NaBr, NaI, KBr, KI, RbBr, RbI, CsBr, CsI, $BeBr_2$, $BeI_2$, $MgBr_2$, $MgI_2$, $CaBr_2$, $CaI_2$, $SrBr_2$, $SrI_2$, $BaBr_2$, $BaI_2$, $ZnBr_2$, $ZnI_2$, $CuBr_2$, $CuI_2$, CuBr, CuI, AgBr, AgI, AuBr, AuI, $NiBr_2$, $NiI_2$, $PdBr_2$, $PdI_2$, $PtBr_2$, $PtI_2$, $CoBr_2$, $CoI_2$, $FeBr_2$, $FeBr_3$, $FeI_2$, $FeI_3$, $MnBr_2$, $MnI_2$, $CrBr_2$, $CrI_2$, $PbBr_2$, $PbI_2$, $SnBr_2$, $SnI_2$, $SnBr_4$, $SnI_4$ and like metal salts;

$NH_4Br$, $NH_4I$, $MeNH_3Br$, $MeNH_3I$, $Me_4NBr$, $Me_4NI$, $Et_4NBr$, $Et_4NI$, $Bu_4NBr$, $Bu_4NI$, $PhMe_3NBr$, $PhMe_3NI$, $PhCH_2NMe_3I$, pyridinium bromide, pyridinium iodide, chloropyridinium iodide, methylpyridinium iodide, cyanopyridinium iodide, bipyridinium iodide, quinolium iodide, isoquinolium iodide, N-methylpyridinium bromide, N-methylpyridinium iodide, N-methylquinolium iodide and like pyridinium salts or ammonium salts;

$Me_4PBr$, $Me_4PI$, $Et_4PI$, $Pr_4PI$, $Bu_4PBr$, $Bu_4PI$, $Ph_4PBr$, $Ph_4PI$ and like phosphonium salts;

sodium fluoride, potassium fluoride, cesium fluoride, ammonium fluoride, tetraethylammonium fluoride, tetrabutylammonium fluoride, polyarylammonium fluoride, sodium chloride, ammonium chloride, sodium hypochlorous acid, sodium chlorite, sodium chlorate, sodium perchlorate, sodium perbromate, sodium periodate and like metal salts or amine salts of hydrogen halides, hypohalous acids, halous acids, halogen acids, or perhalogen acids;

sodium carbonate, potassium carbonate, lithium carbonate, sodium hydrogencarbonate, potassium hydrogencarbonate, lithium hydrogencarbonate, calcium carbonate, magnesium carbonate and like carbonates;

sodium phosphate, potassium phosphate, sodium hydrogenphosphate, sodium dihydrogenphosphate, ammonium phosphate, pyridinium phosphate and like metal salts or amine salts of phosphoric acid;

sodium nitrate, potassium nitrate, ammonium nitrate, pyridinium nitrate and like metal salts or amine salts of nitric acid;

$NaBF_4$, $KBF_4$, $LiBF_4$, $NaSbF_6$, $NaAsF_6$, $NaPF_6$, $NH_4BF_4$, $NH_4SbF_6$, $NH_4PF_6$ and like metal salts or amine salts formed between Lewis acids and hydrogen halide;

tetramethylphosphonium fluoride, tetramethylphosphonium acetate, tetraphenylphosphonium fluoride and like phosphonium salts;

$(C_2H_5)_4NF$, 1-ethyl-3-methylimidazolium fluoride, $(C_2H_5)_3N—(HF)_n$, $(C_2H_5)_4NF—(HF)_n$, $(n-C_4H_9)_3N—(HF)_n$, $(n-C_4H_9)_4NF—(HF)_n$, $BF_3 \cdot Et_2O—(HF)_n$, when (n=1 to 20), and like room temperature molten salts having fluoride anions or HF;

and mixtures thereof.

Examples of the additives used in the present invention include halogen, interhalogen compounds, polyhalides and the like. Specific examples of halogens include iodine, bromine, chlorine, etc. Among those, iodine and bromine are preferable, and iodine is more preferable. Specific examples of the interhalogen compounds include one, two or more members of ClF, BrF, ICl, IBr, $I_2Cl_6$, $ICl_3$, but are not limited to them. Specific examples of the polyhalides include one, two or more members of $LiCl_4I$, $NaCl_4I$, $KCl_4I$, $CsCl_4I$, $RbCl_4I$, $Me_4NCl_4I$, $Et_4NCl_4I$, $Pr_4NCl_4I$, $Bu_4NCl_4I$, $PhNMe_3Cl_4I$, $PhCH_2NMe_3Cl_4I$, $Me_3SCl_4I$, $Cl_8IP$, $KCl_3I_2$, $Me_4NCl_3I_2$, 2,2'-bipyridinium μ-chlorodichlorodiiodate, 2,2'-biquinolinium μ-chlorodichlorodiiodate, $KCl_2I$, $Me_4NCl_2I$, $Me_4NClI_2$, $Et_4NCl_3$, $Ph_4AsCl_3$, $KClF_2$, $Me_4NClF_4$, $CsClF_4$, $CsCl_3FI$, $KBrClI$, $NH_4BrClI$, $Me_4NBrClI$, $Me_4NBrCl_2$, $Bu_4NBrCl_2$, $Me_4NBrCl_2I_2$, $CsBrFI$, $NaBrF_2$, $KBrF_2$, $CsBrF_4$, $Me_4NBrF_4$, $CsBrF_6$, $Me_4NBrF_6$, $Et_4NBr_6Cl$, $CsBr_3$, $Me_4NBr_3$, $Et_4Br_3$, $Bu_4NBr_3$, $PhCH_2NMe_3Br_3$, pyridinium tribromide, $Br_7P$, $CsBrI_2$, $Me_4NBrI_2$, $Me_4NBrI_4$, $Me_4NBrI_6$, $KBr_2Cl$, $Me_4NBr_2Cl$, $Bu_4NBr_2Cl$, $KBr_2I$, $Me_4NBr_2I$, $Bu_4NBr_2I$, 2,2'-bipyridinium μ-bromodibromodiiodate, $NaF_2I$, $KF_2I$, $CsF_4I$, $CsF_6I$, $CsF_8I$, $KI_3$, $CsI_3$, $Me_4NI_3$, $Et_4NI_3$, $Pr_4NI_3$, $Bu_4NI_3$, pyridinium triiodide, $Me_4NI_5$, $Et_4NI_7$, $Me_4NI_9$, $Me_4PBr_3$, $Me_4PI_3$, $Me_4PIBr_2$, $Me_4PICl_2$, $Et_4PI_3$, $Bu_4PI_3$, $Ph_4PI_3$, $Ph_4PBr_3$, $Ph_4PIBr_2$, but are not limited to them.

In the production method of the present invention, $IF_5$ can be used in the amount of 0.2 to 20 moles, preferably 0.3 to 5 moles, and more preferably 0.4 to 2 moles per mole of organic compound having a hydrogen atom and additives can be used in an amount from 0.1 to 10 times (molar ratio) based on the organic compound to react at −70° C. to 200° C., and preferably −20° C. to 100° C.

Use of a reaction solvent is not necessary, but preferably it is used. Specific examples of the reaction solvents include pentane, hexane, heptane, cyclohexane, petroleum ether and like aliphatic solvents, dichloromethane, dichloroethane, chloroform, fluorotrichloromethane, 1,1,2-trichlorotrifluoroethane, 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, heptafluoro-2,3,3-trichlorobutane, 1,1,1,3-tetrachlorotetrafluoropropane, 1,1,1-trichloropentafluoropropane, 1,1,1-trichlorotrifluoroethane, polychlorotrifluoroethylene and like aliphatic halide solvents, methyl formate, ethyl formate, methyl acetate, ethyl acetate, propyl acetate, methyl propionate, γ-butyrolactone, propylene carbonate and like ester solvents, acetonitrile, propionitrile and like nitrile solvents, benzene, chlorobenzene, toluene, dichlorobenzene, fluorobenzene, nitrobenzene and like aromatic solvents, diethylether, dipropylether, tetrahydrofuran and like ether solvents, N,N-dimethyl formamide(DMF), dimethylsulfoxide (DMSO), water, nitromethane, N,N-diethylformamide, N,N-dimethylacetamide, 1-methyl-2-pyrrolidone, 1,3-dimethyl-2-imidazolidinone (DMI), tetramethylurea, 1,3-dimethylpropyleneurea, hexamethylphosphoramide (HMPA), etc. They are used singularly or as a mixture of two or more members.

The order of adding organic compounds and $IF_5$, acids, bases, salts, or additives can be arbitrary so far as long time intervals do not exist between them.

As for postprocessing after the reaction, it is possible to add various kinds of organic or inorganic reducing agents to reduce the excessively oxidized organic compounds, or to reduce $IF_5$ or the oxidative compounds derived from $IF_5$ that remain in an excessive amount.

Specific examples of such reducing agents include zinc powder, tin, tin chloride, iron, aluminium, sodium thiosulphate, butyltinhydride, sodium borohydride, lithium aluminium hydride, etc.; however, as long as they are reductive compounds, the reducing agents are not limited to the above examples.

BEST MODE FOR CARRYING OUT THE INVENTION

The present invention will be explained in more detail referring to the Examples and Comparative Examples given below. However, the scope of the present invention is not limited to these examples.

Example

Organic compounds having hydrogen atoms, which serve as starting materials, are fluorinated using $IF_5$ under the conditions listed in Tables 1 to 6 shown below. The results are shown in Tables 1 to 6.

The reaction conditions of reaction Methods A, B, C, D, D', E, F, G, H, I, and J are described below.

Method A

An $IF_5/Et_3N$-3HF (1:1 molar ratio) solution (1.2 mmol) and a reaction solvent (4 ml) were held in a PFA vessel (15 ml). While stirring at room temperature, a substrate (1.0 mmol) was added hereinto, and allowed to react at a predetermined temperature for a predetermined period of time. After the completion of the reaction, the reaction mixture solution was neutralized by a sodium bicarbonate aqueous solution, and reduced by a 10% sodium thiosulphate aqueous solution. The resultant product was extracted by ether, and isolated and purified using column chromatography. The resultant product was analyzed based on NMR, IR, and MS, and the reaction yield was obtained as the isolation yield of the resultant product against the substrate. In Methods B to E and H to J, postprocessing and analysis after the completion of reaction were conducted in the same manner as that of Method A.

Method B

An $IF_5/Et_3N$-3HF (1:1 molar ratio) solution (1.2 mmol) and a reaction solvent (2 ml) were held in a PFA vessel (15 ml). While stirring at room temperature, a substrate (1.0 mmol) dissolved in a reaction solvent (2 ml) was added hereinto, and allowed to react at a predetermined temperature for a predetermined period of time.

Method C

An $IF_5/Et_3N$-3HF (1:1 molar ratio) solution (1.2 mmol) and a reaction solvent (2 ml) were held in a PFA vessel (15 ml). While stirring at -78° C., a substrate (1.0 mmol) dissolved in a reaction solvent (2 ml) was added, and then allowed to react at room temperature for a predetermined period of time.

Method D

An $IF_5/Et_3N$-3HF (1:1 molar ratio) solution (1.2 mmol) and a solvent (20 ml) were held in a PFA vessel (100 ml). While stirring at room temperature, a substrate (1.0 mmol) dissolved in a reaction solvent (20 ml) was added hereinto using a dropping apparatus in one hour and stirred for one hour.

Method D'

After the completion of the reaction of Method D, 3N of HCl aqueous solution (20 ml) was added to an organic layer washed with water, and stirred using an excessive amount of Zn powder (room temperature, one hour). After filtering solid substances, isolation and purification was performed.

In the Method column on Tables 1 to 6, the asterisk (*) indicates that, instead of the $IF_5/Et_3N$-3HF (1:1 molar ratio) solution, an $IF_5$ (1.2 mmol)/$CH_2Cl_2$ (0.46 g) solution was used.

In the tables, "*2" indicates that, instead of the $IF_5/Et_3N$-3HF (1:1 molar ratio) solution, an $IF_5/Et_4NF$ (1:1 molar ratio) solution was used, and "*3" indicates that instead of the $IF_5/Et_3N$-3HF (1:1 molar ratio) solution, an $IF_5/Et_3N$-5HF (1:1 molar ratio) solution was used.

Method E $IF_5$ (1.2 mmol) and a solvent (4 ml) were held in a PFA vessel (20 ml). While stirring at room temperature, $Et_3N$ (1.2 mmol) was added droppwise. Five minutes later, a substrate (1.0 mmol) was added and stirred at room temperature for three hours. After adding 2-fluoronitrobenzene (1.0 mmol) to the reaction solution as an internal standard, a portion of the reaction solution was taken out and diluted by acetonitrile-d3, and the yield of the fluorinated substance was obtained by $^{19}$F-NMR.

Method F $IF_5/Et_3N$-3HF (1.2 mmol) and a solvent (10 ml) were held in a PFA vessel (100 ml) and heated to 40° C. Then, 10 ml of a solvent solution of a substrate (1.0 mmol) was added thereinto and stirred at 40° C. for 30 minutes. After cooling, fluorobenzene (1.0 mmol) was added to the reaction solution as an internal standard, a portion of the reaction solution was taken out and diluted by acetonitrile-d3, and the yield of the fluorinated substance was obtained by $^{19}$F-NMR.

Method G $IF_5/Et_3N$-3HF (1.5 mmol), iodine (3.0 mmol), and a solvent (30 ml) were held in a PFA vessel (100 ml). Under an ice-cold atmosphere, a substrate (1.0 mmol) dissolved in 10 ml of solvent was added thereinto and stirred under the ice-cold atmosphere for 30 minutes and at room temperature for 30 minutes. After cooling, fluorobenzene (1.0 mmol) was added to the reaction solution as an internal standard, and then a portion of the reaction solution was taken out and diluted by acetonitrile-d3, and the yield of the fluorinated substance was obtained by $^{19}$F-NMR.

Method H

An $IF_5/Et_3N$-3HF (1:1 molar ratio) solution (1.2 mmol) and reaction solvent (8 ml) were held in a PFA vessel (15 ml). While stirring at room temperature, a substrate (1.0 mmol) was added thereinto and allowed to react at a predetermined temperature for a predetermined period of time.

Method I

An $IF_5/Et_3N$-3HF (1:1 molar ratio) solution (1.2 mmol) and a reaction solvent (4 ml) were held in a PFA vessel (15 ml). While stirring at room temperature, a substrate (1.0 mmol) dissolved in a reaction solvent (4 ml) was added thereinto and allowed to react at a predetermined temperature for a predetermined period of time.

Method J

An $IF_5/Et_3N$-3HF (1:1 molar ratio) solution (5.0 mmoles) and a reaction solvent (4 ml) were held in a PFA vessel (15 ml). While stirring at room temperature, a substrate (1.0 mmol) was added thereinto and allowed to react at a predetermined temperature for a predetermined period of time.

The $^{19}$F-NMR signals (F, δ ppm) of IF$_5$/3HF and IF$_5$/Et$_3$N/3HF are shown below.

IF$_5$/3HF (1)

IF$_5$(1F, 55 ppm), (4F, 6.4 ppm), HF(3F, −194 ppm)

IF$_5$/Et$_3$N/3HF (2)

Measuring temperature: 25° C.
One wide single peak was observed at the δ value of −53 ppm.

Measuring temperature: −40° C.
Two wide single peaks were observed at the δ values of 7.5 ppm and −160 ppm. (Integration ratio: approximately 1:1)

Measuring temperature: −60° C.
Three wide single peaks were observed at the δ values of 3 ppm, −154 ppm, and −162 ppm. (Integration ratio: approximately 2:1:1)

From comparison of the $^{19}$F-NMR signals of IF$_5$/3HF and IF$_5$/Et$_3$N/3HF, the compounds generated from IF$_5$/Et$_3$N/3HF have complexes formed therein.

Spectrum data of the compounds obtained by the present invention are shown below. Regarding the compounds for which spectrum data is not shown, it was confirmed that the targeted compounds were obtained by comparing the spectrum data obtained in the Examples of the present invention with the known spectrum data.

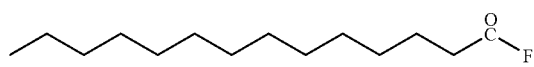

Tetradecanoyl fluoride:
$^1$H-NMR (CDCl$_3$) δ 0.88 (3H, t, J=6.7 Hz), 1.25-1.32 (20H, m), 1.64-1.71 (2H, m), 2.50 (2H, t, J=7.3 Hz);
$^{19}$F-NMR (CDCl$_3$) δ 44.8 (s);
IR (neat, cm$^{-1}$) 2925, 2854, 1845, 1467, 1081.

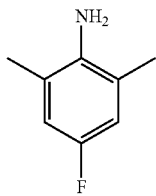

4-Fluoro-2,6-dimethyl-phenylamine:
$^1$H-NMR (CDCl$_3$) δ 2.16 (6H, s), 3.42 (2H, bs), 6.67 (2H, d, J=9.2 Hz);
$^{19}$F-NMR (CDCl$_3$) δ −128.3 (1F, t, J=9.2).

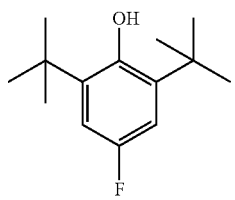

2,6-Di-tert-butyl-4-fluoro-phenol:
$^1$H-NMR (CDCl$_3$) δ: 1.42 (18H, s); 4.94(1H, s); 6.87 (2H, d, J=10.2 Hz);
$^{19}$F-NMR(CDCl$_3$) δ: −124.7 (1F, t, J=10.2);
IR (neat, cm$^{-1}$); 3642; 2961; 1599; 1428; 1236; 1149; 964; 867; 776;
MS m/z: 224 (M$^+$); 209 (M$^+$-Me); 57;
HRMS Calc. for C$_{14}$H$_{21}$OF: m/z 224.1576. Found: m/z 224.1571.

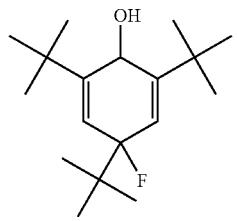

2,4,6-Tri-tert-butyl-4-fluoro-cyclohexa-2,5-dienone:
$^1$H-NMR (CDCl$_3$) δ 0.99 (9H, s), 1.24 (18H, s), 6.63 (2H, d, J=10.5 Hz);
$^{19}$F-NMR(CDCl$_3$) δ −96.6 (1F, t, J=10.3 Hz);
IR (KBr, cm$^{-1}$) 2958, 2873, 1734, 1670, 1138, 1650, 1461, 1364, 1272, 1123, 1073, 965.

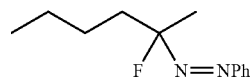

(1-Fluoro-1-methyl-pentyl)-phenyl-diazene:
$^1$H-NMR (CDCl$_3$) δ 0.90 (3H, t, J=7.1 Hz), 1.30-1.55 (4H, m), 1.57 (3H, d, J=20.0 Hz), 168-1.13 (2H, m), 7.47-7.50 (3H, m), 7.74-7.78 (2H, m);
$^{19}$F-NMR(CDCl$_3$) δ −130.1-129.2 (1F, m);
IR (neat, cm$^{-1}$) 2957, 1526, 1455, 1141, 765, 689.

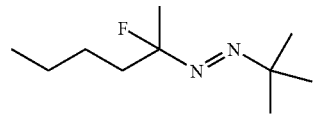

tert-Butyl-(1-fluoro-1-methyl-pentyl)-diazene:
$^1$H-NMR (CDCl$_3$) δ 0.89 (3H, t, J=7.1 Hz), 1.22 (9H, s), 1.23-1.35 (4H, m), 1.39 (3H, d, J=20.0 Hz), 1.68-1.88 (2H, m);
$^{19}$F-NMR(CDCl$_3$) δ −130.9-131.2 (1F, m);
IR (neat, cm$^{-1}$) 2965, 1457, 1364, 1230, 1149, 905.

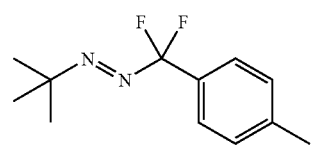

tert-Butyl-(difluoro-p-tolyl-methyl)-diazene:
$^1$H-NMR (CDCl$_3$) δ 1.24 (9H, s), 2.37 (3H, s), 7.22 (2H, d, J=8.1 Hz), 7.44 (2H, d, J=8.1 Hz);
$^{19}$F-NMR(CDCl$_3$) δ −91.1(2F, s);
IR (neat, cm$^{-1}$) 2978, 1809, 1614, 1364, 1288, 1150, 1103, 1039, 1002, 819.

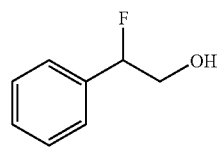

2-Fluoro-2-phenyl-ethanol:
 $^1$H-NMR (CDCl$_3$) δ 1.97 (1H, s), 3.77-3.99 (2H, m), 5.57 (1H, ddd, J=48.8, J=7.8, J=2.9 Hz), 7.34-7.42 (5H, m);
 $^{19}$F-NMR(CDCl$_3$) δ −171.1-171.5 (1F, J=48.8, J=29.9, J=19.9 Hz);
 IR (KBr, cm$^{-1}$) 3376, 3030, 2872, 1495, 1454, 1133, 756, 700.

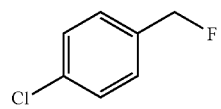

1-Chloro-4-fluoromethyl-benzene:
 $^1$H-NMR (CDCl$_3$) δ 5.31 (2H, d, J=47.6 Hz), 7.31 (2H, d, J=8.3 Hz), 7.37 (2H, d, J=8.3 Hz);
 $^{19}$F-NMR(CDCl$_3$) δ −208.02 (1F, t, J=47.6 Hz);
 IR (neat, cm$^{-1}$) 1601, 1493, 1410, 1376, 1215, 1091, 985, 840, 804.

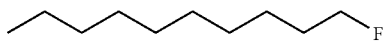

1-Fluoro-decane:
 $^1$H-NMR (CDCl$_3$) δ 0.88 (3H, t, J=6.8 Hz), 1.27-1.40 (14H, m), 1.64-1.74 (2H, m), 4.43 (2H, dt, J=47.6, J=6.1 Hz);
 $^{19}$F-NMR(CDCl$_3$) δ −208.02 (1F, tt, J=47.6, J=25.0 Hz);
 IR (neat, cm$^{-1}$) 2985, 2926, 2856, 1467, 1389, 1046, 1010, 722.

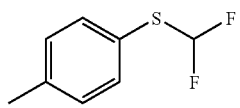

1-Difluoromethylsulfanyl-4-methyl-benzene:
 $^1$H-NMR (CDCl$_3$) 2.37 (3H, s), 6.78 (1H, t, J=57.3 Hz), 7.19(2H, d, J=8.0 Hz), 7.46 (2H, d, J=8.0 Hz);
 $^{19}$F-NMR(CDCl$_3$) δ −92.23 (2F, d, J=57.3 Hz);
 IR (neat, cm$^{-1}$) 2924, 1597, 1494, 1454, 1320, 1296, 1068, 1020, 818, 796.

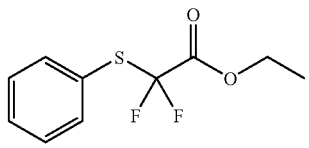

Difluoro-phenylsulfanyl-acetic acid ethyl ester:
 $^1$H-NMR (CDCl$_3$) δ 1.26 (3H, t, J=7.3 Hz), 4.25, (2H, q, J=7.3 Hz), 7.32-7.75 (5H, m);
 $^{19}$F-NMR(CDCl$_3$) δ −82.77(2F, s);
 IR (neat, cm$^{-1}$) 2986, 1766, 1474, 1442, 1372, 1296, 1107, 978, 753, 690.

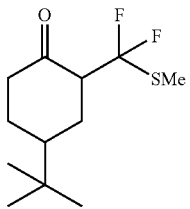

4-tert-Butyl-2-(difluoro-methylsulfanyl-methyl)-cyclohexanone:
 $^1$H-NMR (CDCl$_3$) δ 0.93 (9H, s), 1.25-3.50 (10H, m);
 $^{19}$F-NMR(CDCl$_3$) δ −81.56-74.28(2F, m);
 IR (neat, cm$^{-1}$) 2961, 1714, 1440, 1368, 1330, 1175, 1030, 972.

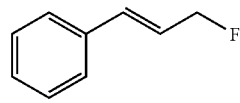

(3-Fluoro-propenyl)-benzene:
 $^1$H-NMR (CDCl$_3$) δ 5.03 (2H, ddd, J=1.2, J=6.1, J=46.8), 6.32-6.42 (1H, m), 6.70 (1H, dd, J=5.1, J=15.9) 7.27-7.42 (5H, m);
 $^{19}$F-NMR(CDCl$_3$) δ −211.09 (1F, ddt, J=5.1, J=12.2, J=46.8 Hz);
 IR (neat, cm$^{-1}$) 3027, 2930, 1726, 1495, 1450, 1377, 1114, 967, 746, 692.

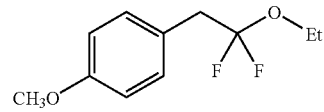

1-(2-Ethoxy-2,2-difluoro-ethyl)-4-methoxy-benzene:
 $^1$H-NMR (CDCl$_3$) δ 1.22 (3H, t, J=7.2 Hz), 3.17 (2H, t, J=11.0 Hz), 3.80 (3H, s), 3.89 (2H, q, J=7.1 Hz), 6.85 (2H, J=8.8 Hz), 7.21 (2H, J=8.8 Hz);
 $^{19}$F-NMR(CDCl$_3$) δ −74.94 (2F, t, J=11.0 Hz);
 IR (neat, cm$^{-1}$) 2987, 2838, 1615, 1517, 1347, 1351, 1247, 1179, 1036, 823.

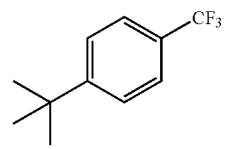

1-tert-Butyl-4-trifluoromethyl-benzene:
 $^1$H-NMR (CDCl$_3$) δ 1.34 (9H, s), 7.49 (2H, d, J=8.6 Hz), 7.55 (2H, d, J=8.6 Hz);
 $^{19}$F-NMR(CDCl$_3$) δ −62.90 (3F, s);
 IR (neat, cm$^{-1}$) 2968, 1617, 1328, 1166, 1115, 1070, 1015, 840, 706.

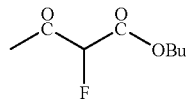

1-Fluoro-3-oxo-butyric acid butyl ester:
$^1$H-NMR (CDCl$_3$) δ 0.95 (3H, t, J=7.3 Hz), 1.36-1.42 (2H, m), 1.66-1.69 (2H, m), 2.35 (3H, t, J=4.2 Hz), 5.22 (2H, d, J=49.6 Hz);
$^{19}$F-NMR(CDCl$_3$) δ −193.66 (1F, dq, J=49.3 Hz, J=4.3 Hz);
IR (neat, cm$^{-1}$) 2964, 2876, 1748, 1735, 1466, 1362, 1261, 1164, 1109, 964.

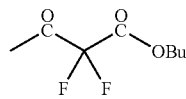

2,2-Difluoro-3-oxo-butyric acid butyl ester:
$^1$H-NMR (CDCl$_3$) δ 0.95 (3H, t, J=7.5 Hz), 1.37-1.44 (2H, m), 1.66-1.73 (2H, m), 2.42 (3H, t, J=1.6 Hz), 4.32 (2H, t, J=6.7 Hz);
$^{19}$F-NMR(CDCl$_3$) δ −114.18 (2F, q, J=1.6);
IR (neat, cm$^{-1}$) 2964, 2876, 1759, 1465, 1362, 1312, 1134, 1056.

2,2-Difluoro-[1,3]dithiane:
$^1$H-NMR (CDCl$_3$) δ 2.07-2.15 (2H, m), 3.13-3.17 (2H, m);
$^{19}$F-NMR(CDCl$_3$) δ −63.95 (2F, s);
$^{13}$C-NMR(CDCl$_3$) δ 23.43, 29.98, 130.77 (t, J$_{C-F}$=301.1 Hz);
IR (neat, cm$^{-1}$) 2926, 1677, 1422, 1282, 1081, 998, 921, 873, 811.

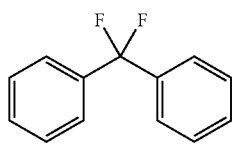

Difluoro-diphenyl-methane:
$^1$H-NMR (CDCl$_3$) δ 7.39-7.52 (10H, m);
$^{19}$F-NMR(CDCl$_3$) δ −89.40 (2F, s);
IR (neat, cm$^{-1}$) 3067, 1453, 1273, 1223, 1026, 956, 771, 696, 647;
MS m/z: 204 (M$^+$); 127, 77;
HRMS: Calc. for C$_{13}$H$_{10}$F$_2$: m/z 204.0751. Found: m/z 204.0755.

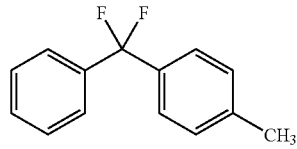

Difluoro-(4-methylphenyl)-phenyl-methane:
$^1$H-NMR (CDCl$_3$) δ 2.37 (3H, s), 7.19-7.51 (9H, m);
$^{19}$F-NMR(CDCl$_3$) δ −88.78 (2F, s);
IR (neat, cm$^{-1}$) 3068, 2927, 2867, 1450, 1276, 1235, 1046, 958, 619, 582;
MS m/z: 218 (M$^+$) 141, 65;
HRMS: Calc. for C$_{14}$H$_{12}$F$_2$: m/z 218.0907. Found: m/z 218.0913.

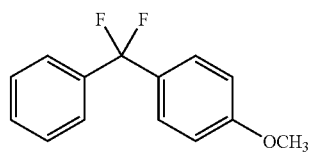

Difluoro-(4-methoxyphenyl)-phenyl-methane:
$^1$H-NMR (CDCl$_3$) δ 2.80 (3H, s), 6.89-7.51 (9H, m);
$^{19}$F-NMR(CDCl$_3$) δ −87.41 (2F, s);
IR (neat, cm$^{-1}$) 3061, 2969, 2936, 2838, 1616, 1514, 1452, 1277, 1224, 1056, 957, 616, 588;
MS m/z: 234 (M$^+$); 212, 135, 77;
HRMS: Calc. for C$_{14}$H$_{12}$F$_2$O: m/z 234.0856. Found: m/z 234.0856.

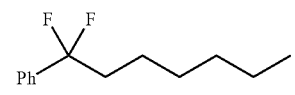

(1,1-Difluoro-heptyl)-benzene:
$^1$H-NMR (CDCl$_3$) δ 0.86 (3H, t, J=6.8 Hz), 1.26-1.33 (6H, m), 1.37-1.44 (2H, m), 2.05-2.17 (2H, m), 7.40-7.45 (5H, m);
$^{19}$F-NMR(CDCl$_3$) δ −89.40 (2F, t, J=16.5);
IR (neat, cm$^{-1}$) 2932, 2859, 1452, 1327, 1168, 1018, 966, 763, 698;
MS m/z: 212 (M$^+$); 192, 169, 135, 127, 122, 91, 77;
HRMS: Calc. for C$_{13}$H$_{18}$F$_2$: m/z 212.1377. Found: m/z 212.1374.

1-Difluoromethyl-4-methoxy-benzene:
$^1$H-NMR (CDCl$_3$) δ 3.77 (3H, s), 6.32 (1H, t, 56 Hz), 6.87-7.38 (4H, d, 9 Hz);
$^{19}$F-NMR(CDCl$_3$) δ −108.82 (1H, d, 57 Hz);
IR (neat, cm$^{-1}$) 3011, 2966, 2842, 1617, 1520, 1308, 1176, 1069, 839;
MS m/z: 158 (M$^+$); 139, 127, 115, 108, 95, 77;

HRMS; Calc. for $C_8H_9F_2O$: m/z 158.0543. Found: m/z 158.0549.

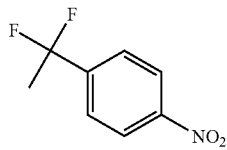

1-(1,1-Difluoro-ethyl)-4-nitro-benzene:
$^1$H-NMR (CDCl$_3$) δ 1.96 (3H, t, 18 Hz), 7.69-8.31 (4H, q, 18 Hz);
$^{19}$F-NMR(CDCl$_3$) δ −89.71-(−89.56) (2F, q, 18 Hz);
IR (neat, cm$^{-1}$) 3122, 3089, 3010, 2927, 2862, 1937, 1798, 1612, 634, 476;
MS m/z: 187 (M$^+$), 172, 141, 101, 91;
HRMS; Calc. for $C_8H_7F_2NO_2$: m/z 187.0445. Found: m/z 187.0449.

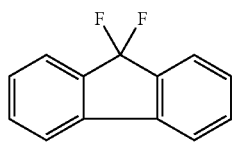

9,9-Difluoro-9H-fluorene:
$^1$H-NMR (CDCl$_3$) δ 7.32-7.63 (8H, m);
$^{19}$F-NMR(CDCl$_3$) δ −112.14 (2F, s);
IR (neat, cm$^{-1}$) 1610, 1492, 1453, 1261, 1209, 1165, 939, 653, 585, 423;
MS m/z: 202 (M$^+$); 183, 152, 101, 92, 76;
HRMS: Calc. for $C_{13}H_8F_2$: m/z 202.0594. Found: m/z 202.0594.

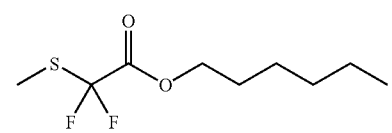

Difluoro-methylsulfanyl-acetic acid hexyl ester:
$^1$H-NMR (400 MHz, CDCl$_3$): δ 0.90 (t, 3H, J=6.8 Hz), 1.25-1.42 (m, 6H), 1.69-1.76 (m, 2H), 2.35 (s, 3H), 4.30 (t, 2H, J=6.6 Hz);
$^{19}$F-NMR (90 MHz, CDCl$_3$): δ −86.25 (s, 2F);
IR (neat, cm$^{-1}$): 2961.16, 2935.13, 2860.88, 1769.37, 1293.04, 1123.33, 1000.87;
MS m/z: 226 (M$^+$), 142, 129, 97, 85, 43;
HRMS; Calc. for $C_{13}H_8F_2$: m/z 226.0839. Found: m/z 226.0846.

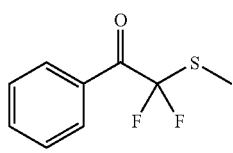

2,2-Difluoro-2-methylsulfanyl-1-phenyl-ethanone:
$^1$H-NMR (400 MHz, CDCl$_3$): δ 2.37 (s, 3H), 7.49-8.15 (m, 5H);
$^{19}$F-NMR (90 MHz, CDCl$_3$): δ −82.29 (s, 2F);
IR (neat, cm$^{-1}$): 0.1704, 1598, 1449, 1270, 1133, 1063, 1004;
MS m/z: 202 (M$^+$), 105, 77, 51.
HRMS; Calc. for $C_{13}H_8F_2$: m/z 202.0264. Found: m/z 202.0266.

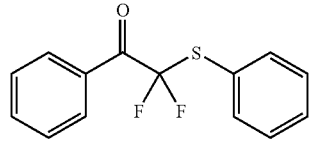

2,2-Difluoro-1-phenyl-2-phenylsulfanyl-ethanone:
$^1$H-NMR (400 MHz, CDCl$_3$): δ 7.37-8.14 (m, 10H);
$^{19}$F-NMR (90 MHz, CDCl$_3$): δ −77.78 (s, 2F);
IR (neat, cm$^{-1}$): 1704, 1598, 1449, 1272, 1132, 986, 852, 750, 712, 688;
MS m/z: 264(M$^+$), 105, 77, 51;
HRMS; Calc. for $C_{13}H_8F_2$: m/z 264.0420 m/z 264.0426.

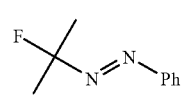

(1-Fluoro-1-methyl-ethyl)-phenyl-diazene:
$^1$H-NMR (CDCl$_3$) δ 1.60 (6H, d, J=19.8 Hz), 7.47 (3H, m), 7.77(2H, m);
$^{19}$F-NMR(CDCl$_3$) δ −120.96 (1F, seventet, J=19.8 Hz);
IR (neat, cm$^{-1}$) 2292, 1526, 1455, 1366, 1178, 1145, 908, 756, 689.

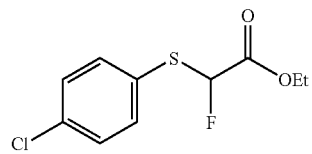

$^1$H-NMR (400 MHz, CDCl$_3$): δ 1.21 (t, 3H, J=7.1 Hz), 4.16 (q, 2H, J=7.2 Hz), 6.03 (d, 1H, J=51.7 Hz), 7.34 (d, 2H, J=8.5 Hz), 7.49 (d, 2H, J=8.5 Hz)
$^{19}$F-NMR (400 MHz, CDCl$_3$): δ −159.40 (d, 2F, J=51.7 Hz)
MS: 248(M$^+$), 175, 108, 75
$C_{10}H_{10}O_2FSCl$, Measured Mass 248.0093, Calculated Mass 248.0074

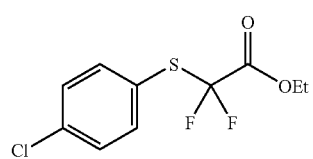

$^1$H-NMR (400 MHz, CDCl$_3$): δ 1.30 (t, 3H, J=7.2 Hz), 4.29 (q, 2H, J=7.2 Hz), 7.38 (d, 2H, J=8.5 Hz), 7.55 (d, 2H, J=8.5 Hz)
$^{19}$F-NMR (400 MHz, CDCl$_3$): δ −82.66 (s, 1F)

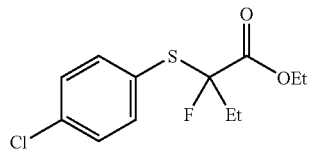

¹H-NMR (400 MHz, CDCl₃): δ 1.06 (t, 3H, J=7.3 Hz), 1.10 (t, 3H, J=7.1 Hz), 2.10-2.36 (m, 2H), 3.97-4.08 (m, 2H), 7.31 (d, 2H, J=8.5 Hz), 7.48 (d, 2H, J=8.5 Hz)
¹⁹F-NMR (400 MHz, CDCl₃): δ −138.53-138.43 (m, 1F)

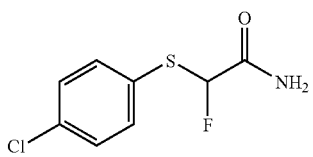

¹H-NMR (400 MHz, CDCl₃): δ 5.58 (bs, 1H), 6.03 (bs, 1H), 6.07 (d, 1H, J=52.7 Hz), 7.35 (d, 2H, J=8.3 Hz), 7.53 (d, 2H, J=8.3 Hz)
¹⁹F-NMR (400 MHz, CDCl₃): δ −155.46 (d, 1F, J=52.7 Hz)

¹H-NMR (400 MHz, CDCl₃): δ 1.24 (d, 3H, J=6.3 Hz), 1.25 (d, 3H, J=6.3 Hz), 1.35 (d, 3H, J=6.8 Hz), 1.42 (d, 3H, J=6.8 Hz), 3.42-3.49 (m, 1H), 4.16-4.22 (m, 1H), 6.16 (d, 1H, J=55.9 Hz), 7.33 (d, 2H, J=8.3 Hz), 7.50 (d, 2H, J=8.3 Hz)
¹⁹F-NMR (400 MHz, CDCl₃): δ −152.36 (d, 1F, J=55.9 Hz)

¹H-NMR (400 MHz, CDCl₃): δ 1.22 (d, 6H, J=6.59 Hz), 1.43 (d, 6H, J=6.83 Hz), 3.47-3.55 (m, 1H), 4.40-4.46 (m, 1H), 7.37 (d, 2H, J=8.5 Hz), 7.56 (d, 2H, J=8.5 Hz)
¹⁹F-NMR (400 MHz, CDCl₃): δ −73.46 (s, 2F)

¹H-NMR (400 MHz, CDCl₃) δ 2.55-2.60 (m, 1H), 2.74-2.86 (m, 1H), 4.32-4.45 (m, 2H), 7.36 (d, 2H, J=8.5 Hz), 7.51 (d, 2H, J=8.5 Hz)
¹⁹F-NMR (400 MHz, CDCl₃): δ −135.76 (d, 1H, J=15.9 Hz)

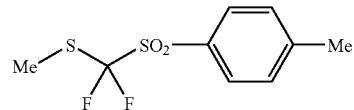

¹H-NMR (400 MHz, CDCl₃): δ 2.49 (s, 3H), 2.53 (s, 3H), 7.42 (d, 2H, J=8.1 Hz), 7.88 (d, 2H, J=8.1 Hz)
¹⁹F-NMR (400 MHz, CDCl₃): δ −83.83 (s, 2H)

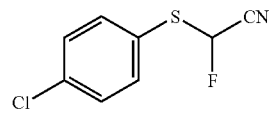

¹H-NMR (400 MHz, CDCl₃) δ 6.18 (d, 1H, J=48.8 Hz), 7.43 (d, 2H, J=8.5 Hz), 7.57 (d, 2H, J=8.5 Hz)
¹⁹F-NMR (400 MHz, CDCl₃): δ −153.90 (d, 1H, J=48.8 Hz)
MS: 201(M+), 143, 63
C₈H₅NFSCl, Measured Mass 200.9798, Calculated Mass 200.9815

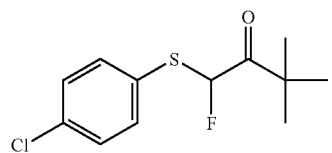

¹H-NMR (400 MHz, CDCl₃): δ 1.24 (s, 9H), 6.29 (d, 1H, J=54.2 Hz), 7.34 (d, 2H, J=8.5 Hz), 7.48 (d, 2H, J=8.5 Hz)
¹⁹F-NMR (400 MHz, CDCl₃): δ −157.40 (d, 1F, J=54.2 Hz)
MS: 260(M+), 175, 108, 57
C₁₂H₁₄OFSCl, Measured Mass 260.0421, Calculated Mass 260.0438

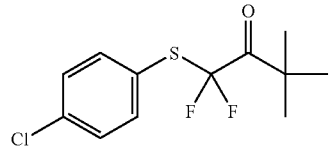

¹H-NMR (400 MHz, CDCl₃) δ 1.29 (s, 9H), 7.37 (d, 2H, J=8.5 Hz), 7.53 (d, 2H, J=8.5 Hz)
¹⁹F-NMR (400 MHz, CDCl₃): δ −77.61 (s, 2F)

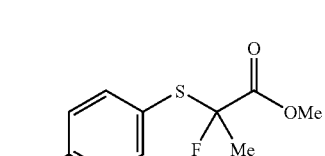

¹H-NMR (400 MHz, CDCl₃): δ 1.91 (d, 3H, J=18.3 Hz), 3.60 (s, 3H), 7.33 (d, 2H, J=8.5 Hz), 7.47 (d, 2H, J=8.5 Hz)
¹⁹F-NMR (400 MHz, CDCl₃): δ −127.24 (q, 1F, J=18.3 Hz)

TABLE 1

| Example | Material | Temp. (° C.) | Period of time (h) | Solvent | Method | Resultant product | Yield (%) |
|---|---|---|---|---|---|---|---|
| 1 | nC$_{13}$H$_{27}$—COOH | r.t. | 12 | CH$_2$Cl$_2$ | A | nC$_{13}$H$_{27}$—COF | 75 |
| 2 | nC$_{13}$H$_{27}$—COOH | 125 | 12 | No solvent | A | nC$_{13}$H$_{27}$—COF | 65 |
| 3 | nC$_{10}$H$_{21}$—OH | 80 | 48 | Heptane | A | nC$_{10}$H$_{21}$—F | 32 |
| 4 | 4-Cl-C$_6$H$_4$-CH$_2$OH | r.t. | 1 | CH$_2$Cl$_2$ | A | 4-Cl-C$_6$H$_4$-CH$_2$F | 83 |
| 5 | 4-Cl-C$_6$H$_4$-CH$_2$OH | r.t. | 1 | CH$_2$Cl$_2$ | A* | 4-Cl-C$_6$H$_4$-CH$_2$F | 6 |
| 6 | 4-Me-C$_6$H$_4$-SCH$_3$ | 100 | 1 | Heptane | A | 4-Me-C$_6$H$_4$-SCHF$_2$ | 50 |
| 7 | PhCOCH$_2$SCH$_3$ | 74 | 1 | Heptane | A | PhCOCF$_2$SCH$_3$ | 82 |
| 8 | PhS-CH$_2$-COOEt | 70 | 1 | Heptane | A* | PhCOCF$_2$SCH$_3$ | 51 |
| 9 | PhS-CH$_2$-COOEt | 63 | 4 | Hexane | A | PhS-CF$_2$-COOEt | 59 |
| 10 | PhS-CH$_2$-COPh | 63 | 4 | Hexane | A | PhS-CF$_2$-COPh | 45 |
| 11 | 4-tBu-2-(bis(methylthio)methylene)cyclohexan-1-one | r.t. | 3 | Hexane | A | 4-tBu-2-(MeS-CF$_2$-)cyclohexan-1-one | 60 |
| 12 | styrene oxide | r.t. | 5 | CH$_2$Cl$_2$ | B | PhCHF-CH$_2$OH | 75 |
| 13 | styrene oxide | r.t. | 5 | CH$_2$Cl$_2$ | B* | PhCHF-CH$_2$OH | 62 |
| 14 | PhCOPh | 100 | 12 | No solvent | A | PhCF$_2$Ph | 23 |
| 15 | (Ph)$_2$C=NNH$_2$ | r.t. | 1 | EtOAc | D | PhCF$_2$Ph | 70 |
| 16 | (Me)$_2$C=N—NHPh | r.t. | 0.5 | EtOAc | C | (Me)$_2$CF—N=NPh | 51 |
| 17 | Bu(Me)C=N—NHPh | r.t. | 0.5 | EtOAc | C | Bu(Me)CF—N=N—Ph | 80 |

TABLE 2

| Example | Material | Temp. (°C.) | Period of time (h) | Solvent | Method | Resultant product | Yield (%) |
|---|---|---|---|---|---|---|---|
| 18 | Bu-C(CH₃)=N-NH-tBu | r.t. | 0.5 | EtOAc | C | Bu-C(CH₃)(F)-N=N-tBu | 52 |
| 19 | Tol-CH=N-NH-tBu | r.t. | 1 | CH₂Cl₂ | D | Tol-CF₂-N=N-tBu | 45 |
| 20 | phNHNH₂ | r.t. | 0.5 | CH₂Cl₂ | A | PhF, PhI | PhF(30) PhI(40) |
| 21 | 2,6-di-tert-butylphenol | r.t. | 4 | CH₂Cl₂ | D' | 4-fluoro-2,6-di-tert-butylphenol | 50 |
| 22 | 2,6-dimethylaniline | r.t. | 4 | CH₂Cl₂ | D' | 4-fluoro-2,6-dimethylaniline | 27 |
| 23 | CH₃COCH₂COOEt | r.t. | 3 | CH₂Cl₂ | E | CH₃COCHFCOOEt | 11 |
|   |   |   |   |   |   | CH₃COCF₂COOEt | 6 |
| 24 | CH₃COCH₂COOBu | 40 | 1 | CH₂Cl₂ | A | CH₃COCHFCOOBu | 71 |
| 25 | CH₃COCH₂COOBu | 60 | 24 | Hexane | A | CH₃COCF₂COOBu | 25 |
| 26 | PhCH=CHCH₂OH | r.t. | 1 | Hexane | D | PhCH=CHCH₂F | 45 |
|   |   |   |   |   |   | PhCHF—CH=CH₂ | 22 |
| 27 | 2-naphthol | 40 / 0 / r.t. | 0.5 / 0.5 / 0.5 | (CH₂Cl)₂ / CH₂Cl₂ | F / G | 1,1-difluoro-2(1H)-naphthalenone | 35 / 56 |

TABLE 3

| Example | Material | Temp. (° C.) | Period of time (h) | Solvent | Method | Resultant product | Yield (%) |
|---|---|---|---|---|---|---|---|
| 28 | (diphenyl 1,3-dithiolane) | r.t. | 0.5 | $CH_2Cl_2$ | A | $Ph_2CF_2$ | 91 |
| 29 | (diphenyl 1,3-dithiolane) | r.t. | 0.5 | $CH_2Cl_2$ | A*[2] | $Ph_2CF_2$ | 56 |
| 30 | (pyridyl phenyl 1,3-dithiolane) | r.t. | 0.5 | $CH_2Cl_2$ | A* | difluoro(pyridyl)(phenyl)methane | 64 |
| 31 | (diphenyl 1,3-dithiolane) | r.t. | 0.5 | $CH_2Cl_2$ | A*[3] | $Ph_2CF_2$ | 62 |
| 32 | (phenyl p-tolyl 1,3-dithiolane) | r.t. | 0.5 | $CH_2Cl_2$ | A | difluoro(phenyl)(p-tolyl)methane | 99 |
| 33 | (phenyl p-tolyl 1,3-dithiolane) | r.t. | 0.5 | $CH_2Cl_2$ | A | difluoro(phenyl)(p-methoxyphenyl)methane | 87 |
| 34 | (phenyl hexyl 1,3-dithiolane) | r.t. | 0.5 | $CH_2Cl_2$ | A | $PhCF_2CH_2(CH_2)_4CH_3$ | 64 |
| 35 | (4-methoxyphenyl 1,3-dithiolane) | r.t. | 0.5 | $CH_2Cl_2$ | A | $H_3CO$-C$_6$H$_4$-CHF$_2$ | 58 |
| 36 | (fluorene dithiolane) | r.t. | 0.5 | $CH_2Cl_2$ | A | 9,9-difluorofluorene | 96 |
| 37 | (4-nitrophenyl methyl 1,3-dithiolane) | r.t. | 2 | AcOEt | J | $O_2N$-C$_6$H$_4$-CF$_2$CH$_3$ | 30 |

TABLE 4

| Example | Material | Temp. (° C.) | Period of time (h) | Solvent | Method | Resultant product | Yield (%) |
|---|---|---|---|---|---|---|---|
| 38 | 1,3-dithiane | r.t. | 2.5 | AcOEt | H | 2,2-difluoro-1,3-dithiane | 51 |
| 39 | [4-tBu-C$_6$H$_4$-C(1,3-dithiolane)-S-CH$_2$-]$_2$ | r.t. | 0.5 | CH$_2$Cl$_2$ | I | 4-tBu-C$_6$H$_4$-CF$_3$ | 91 |
| 40 | H$_3$CS-CH$_2$-C(O)-OCH$_2$(CH$_2$)$_4$CH$_3$ | r.t. | 126 | Heptane | A | H$_3$CS-CF$_2$-C(O)-OCH$_2$(CH$_2$)$_4$CH$_3$ | 78 |
| 41 | H$_3$CS-CH$_2$-C(O)-OCH$_2$(CH$_2$)$_4$CH$_3$ | 40 | 48 | Heptane | A | H$_3$CS-CF$_2$-C(O)-OCH$_2$(CH$_2$)$_4$CH$_3$ | 73 |
| 42 | H$_3$CS-CH$_2$-C(O)-OCH$_2$(CH$_2$)$_4$CH$_3$ | 60 | 7 | Heptane | A | H$_3$CS-CF$_2$-C(O)-OCH$_2$(CH$_2$)$_4$CH$_3$ | 81 |
| 43 | H$_3$CS-CH$_2$-C(O)-OCH$_2$(CH$_2$)$_4$CH$_3$ | 40 | 32 | CHCl$_3$ | A | H$_3$CS-CF$_2$-C(O)-OCH$_2$(CH$_2$)$_4$CH$_3$ | 68 |
| 44 | H$_3$CS-CH$_2$-C(O)-OCH$_2$(CH$_2$)$_4$CH$_3$ | r.t. | 6 | Heptane | A* | H$_3$CS-CF$_2$-C(O)-OCH$_2$(CH$_2$)$_4$CH$_3$ | 59 |
| 45 | PhCSPh | r.t. | 1 | CH$_2$Cl$_2$ | I | PhCF$_2$Ph | 72 |
| 46 | 4-H$_3$CO-C$_6$H$_4$-CH$_2$-C(=S)-OEt | r.t. | 2.5 | AcOEt | H | 4-H$_3$CO-C$_6$H$_4$-CH$_2$-CF$_2$-OEt | 97 |
| 47 | 2,4,6-tri-tert-butylphenol | r.t. | 1 | CH$_2$Cl$_2$ | A*² | 4-fluoro-2,4,6-tri-tert-butylcyclohexa-2,5-dienone | 60 |
| 48 | EtOOC-C$_6$H$_{10}$=N-NH$_2$ | r.t. | 1 | CH$_2$Cl$_2$ | A | EtOOC-C$_6$H$_{10}$-CF$_2$ | 13 |

TABLE 4-continued

| Example | Material | Temp. (°C.) | Period of time (h) | Solvent | Method | Resultant product | Yield (%) |
|---|---|---|---|---|---|---|---|
| 49 | 4-chlorobenzyl alcohol (Cl-C6H4-CH2OH) | r.t. | 0.5 | Hexane | A*2 | 4-chlorobenzyl fluoride (Cl-C6H4-CH2F) | 47 |

TABLE 5

| Example | Material | Temp. (°C.) | Period of time (h) | Solvent | Method | Resultant product | Yield (%) |
|---|---|---|---|---|---|---|---|
| 50 | 4-ClC6H4-S-CH2-C(O)OEt | 40 | 8 | Hexane | A | 4-ClC6H4-S-CHF-C(O)OEt | 75 |
|  |  |  |  |  |  | 4-ClC6H4-S-CF2-C(O)OEt | 15 |
| 51 | 4-ClC6H4-S-CH2-C(O)OEt | 80 | 72 | Heptane | A | 4-ClC6H4-S-CF2-C(O)OEt | 58 |
| 52 | 4-ClC6H4-S-CH(Et)-C(O)OEt | 40 | 36 | Hexane | A | 4-ClC6H4-S-CF(Et)-C(O)OEt | 82 |
| 53 | 4-ClC6H4-S-CH(Me)-C(O)OMe | 40 | 9 | Hexane | A | 4-ClC6H4-S-CF(Me)-C(O)OMe | 89 |
| 54 | 3-(4-chlorophenylthio)-dihydrofuran-2(3H)-one | 40 | 4 | Hexane | A | 3-fluoro-3-(4-chlorophenylthio)-dihydrofuran-2(3H)-one | 65 |
| 55 | 4-ClC6H4-S-CH2-C(O)-C(CH3)3 | 40 | 2 | Hexane | A | 4-ClC6H4-S-CHF-C(O)-C(CH3)3 | 91 |
|  |  |  |  |  |  | 4-ClC6H4-S-CF2-C(O)-C(CH3)3 | 4 |

TABLE 5-continued
| Example | Material | Temp. (° C.) | Period of time (h) | Solvent | Method | Resultant product | Yield (%) |
|---|---|---|---|---|---|---|---|
| 56 | 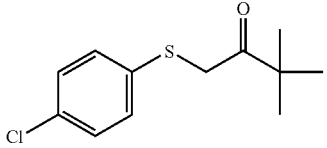 | 80 | 72 | Heptane | A | 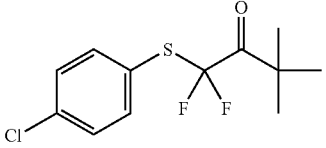 | 84 |
| 57 | 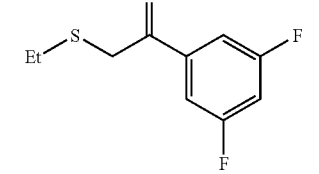 | 40 | 6 | Heptane | A | 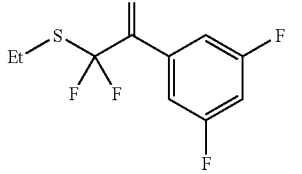 | 79 |
TABLE 6
| Example | Material | Temp. (° C.) | Period of time (h) | Solvent | Method | Resultant product | Yield (%) |
|---|---|---|---|---|---|---|---|
| 58 | 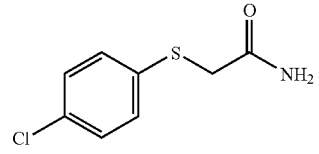 | 40 | 4 | Hexane | A | 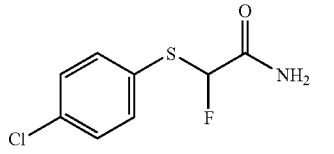 | 71 |
|  |  |  |  |  |  | 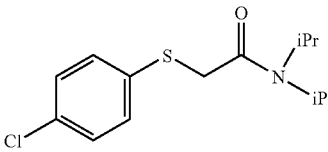 | 7 |
| 59 | 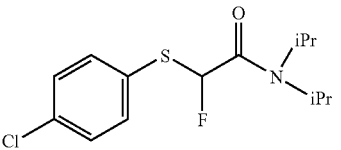 | 40 | 5 | Hexane | A | 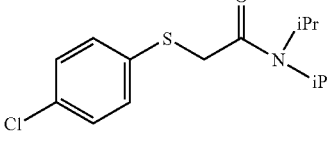 | 88 |
| 60 | 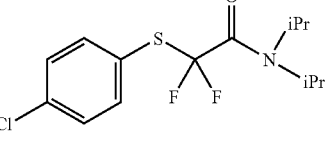 | 80 | 96 | Heptane | A | 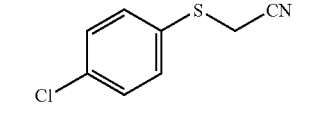 | 83 |
| 61 | 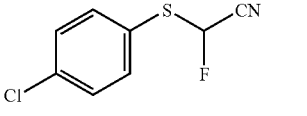 | 40 | 5 | Hexane | A | 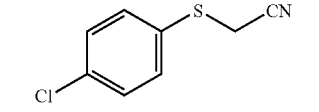 | 82 |
| 62 | 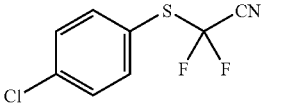 | 80 | 90 | Heptane | A | 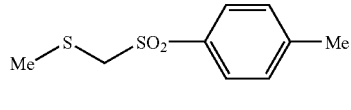 | 76 |
| 63 | 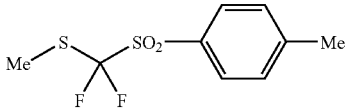 | 60 | 24 | Hexane | A |  | 88 |

In Tables 1 to 6 shown above, "Tol" represents a tolyl group ($CH_3$—$C_6H_4$—), "Ph" represents a phenyl group, "Et" represents an ethyl group, "Me" represents a methyl group, "Bu" represents a butyl group, "Ac" represents an acetyl group, and "iPr" represents an isopropyl group.

As described above, according to the present invention, it is possible to fluorinate various kinds of organic compounds having hydrogen atoms and to obtain corresponding fluorine compounds.

INDUSTRIAL APPLICABILITY

According to the present invention, using $IF_5$, which is an industrially available, nonexplosive, and easy to handle liquid having a boiling point at 100.5° C. and a melting point at 9.4° C., it is possible to fluorinate various kinds of organic compounds having hydrogen atoms and to obtain corresponding fluorine compounds.

The invention claimed is:

1. A fluorinating agent for use in fluorinating an organic compound having hydrogen atoms, which comprises $IF_5$, HF, and an organic base and/or a room temperature molten salt.

2. A fluorinating agent for use in fluorinating an organic compound having hydrogen atoms, which comprises $IF_5$ and a room temperature molten salt.

3. A fluorinating agent for use in fluorinating an organic compound having hydrogen atoms, which comprises $IF_5$ and at least one member selected from the group consisting of bases and salts.

4. A fluorinating agent for use in fluorinating an organic compound having hydrogen atoms, which comprises $IF_5$, HF, and triethylamine.

5. A fluorinating agent according to claim 1, which comprises $IF_5$, HF and an organic base.

6. A fluorinating agent according to claim 1, wherein the organic base is an organic amine.

7. A fluorinating agent according to claim 6, wherein the organic base is an aliphatic amine.

8. A fluorinating agent according to claim 7, wherein the organic base is triethylamine.

9. A fluorinating agent according to claim 1, which comprises $IF_5$, HF, and a room temperature molten salt.

* * * * *